USOO5462941A

United States Patent [19]

Iwase et al.

[11] Patent Number: 5,462,941
[45] Date of Patent: Oct. 31, 1995

[54] 3,6-DISUBSTITUTED PYRADAZINE DERIVATIVES

[75] Inventors: Norimichi Iwase, Kanagawa; Yasuhiro Morinaka, Ibaraki; Yoshikuni Tamao, Tokyo; Toshiji Kanayama; Kumi Yamada, both of Kanagawa, all of Japan

[73] Assignee: Mitsubishi Chemical Corporation, Tokyo, Japan

[21] Appl. No.: 215,426

[22] Filed: Mar. 21, 1994

Related U.S. Application Data

[62] Division of Ser. No. 950,947, Sep. 25, 1992, Pat. No. 5,324,727.

[30] Foreign Application Priority Data

Sep. 26, 1991 [JP] Japan .................................. 3-247647
Dec. 18, 1991 [JP] Japan .................................. 3-335277
Sep. 8, 1992 [JP] Japan .................................. 4-239545

[51] Int. Cl.[6] .................. A61K 31/50; C07D 237/34; C07D 247/02; C07D 409/04
[52] U.S. Cl. .............................................. 514/248; 544/237
[58] Field of Search ............................. 544/237; 514/248

[56] References Cited

U.S. PATENT DOCUMENTS

4,002,617 1/1977 Eiden et al. .............................. 260/240
5,089,494 2/1992 Iwase et al. .............................. 514/248

FOREIGN PATENT DOCUMENTS

0159652A2 10/1985 European Pat. Off. .
0449203A1 10/1991 European Pat. Off. .
2021195 11/1970 Germany .
49-55681 5/1974 Japan .
50-84585 7/1975 Japan .
50-100072 8/1975 Japan .
56-53660 5/1981 Japan .
56-53659 5/1981 Japan .
57-48972 3/1982 Japan .
57-167974 10/1982 Japan .
60-218377 11/1985 Japan .
60-243074 12/1985 Japan .
2-129181 5/1990 Japan .
2-129182 5/1990 Japan .
2-129183 5/1990 Japan .
2-129180 5/1990 Japan .
3-106872 5/1991 Japan .
3-106873 5/1991 Japan .
3-106874 5/1991 Japan .
3-106875 5/1991 Japan .
1293565 10/1972 United Kingdom .
1303061 1/1973 United Kingdom .
2063249 6/1981 United Kingdom .

OTHER PUBLICATIONS

Holava, Jr. et al., Journal of Medicinal Chemistry, vol. 12, No. 3, May, 1969, pp. 555–556.
Robba, Chemical Abstracts, vol. 66 (1967) p. 8908 Abstract No. 95066a.
Morishita Pharmaceutical, Patent Abstracts of Japan, vol. 14, No. 356(C–745) (4299) 2 Aug. 1990 JP–A–2129181; JP–A–2129182; JP–A–2129180; JP–A–2129183.
Mitsubishi Yuka, Patent Abstracts of Japan, vol. 5, No. 114 (C–64)(786) 23 Jul. 1981 for JP–A–56–53659.
Morishita Pharmaceutical, patent Abstracts of Japan, vol. 15, No. 293 (C–853) (4821) 25 Jul. 1991 for JP–A–3106873.

*Primary Examiner*—Mark L. Berch
*Attorney, Agent, or Firm*—Wenderoth, Lind & Ponack

[57] ABSTRACT

A 3,6-disubstituted pyridazine derivative having excellent platelet agglutination inhibitory effects. It is useful for a preventive medicine or a therapeutic medicine for a cerebrovascular disorder such as cerebral thrombosis and cerebral embolism, an ischemic heart disease such as myocardial infarction, and a circulation disorder such as peripheral circulation disorder. A pharmaceutical composition containing a compound of the present invention as an effective ingredient and a process for preparing the same are also disclosed. The compound has the formula (I)

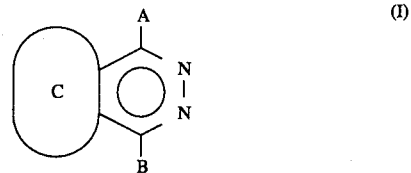

wherein A represents an alkyl group having 3 to 6 carbon atoms; a cycloalkyl group having 5 to 7 carbon atoms; a phenyl group, a thienyl group, a furyl group, a thiazolyl group, a phenoxy group, a phenylalkyl group having 7 to 9 carbon atoms, a phenylthio group, a 5–6 membered saturated heterocyclic group containing one or more nitrogen atoms, a pyridyl group or an imidazolyl group each of which may have at least one substituent selected from the group consisting of an alkyl group having 1 to 4 carbon atoms, an alkoxy group having 1 to 4 carbon atoms and a halogen atom; B represents (a) —NH—D wherein D represents

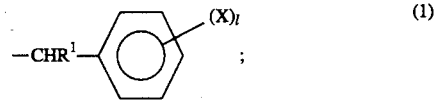

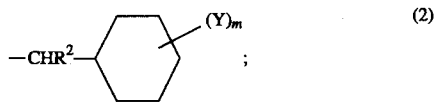

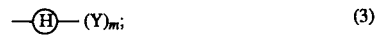

(4) —CH$^3$R$^4$; or (5) an alkyl group having 3 to 8 carbon atoms; or

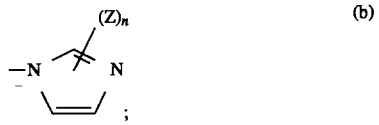

and the ring C represents a benzene ring.

12 Claims, No Drawings

3,6-DISUBSTITUTED PYRADAZINE DERIVATIVES

This application is a division of application Ser. No. 07/950,947, filed Sep. 25, 1992 (now U.S. Pat. No. 5,324, 727).

BACKGROUND OF THE INVENTION

1. Field of the Invention

The present invention relates to 3,6-disubstituted pyridazine derivatives and, more particularly, to 3,6-disubstituted pyridazine derivatives which have platelet agglutination inhibitory action and, hence, are useful as a preventive medicine or a therapeutic medicine for a cerebrovascular disorder such as cerebral thrombosis and cerebral embolism, an ischemic heart disease such as myocardial infarction, and a circulation disorder such as a peripheral circulation disorder. The present invention also relates to optical antipodes of such 3,6-disubstituted pyridazine derivatives and pharmaceutically acceptable acid-addition salts thereof.

2. Description of the Prior Art

Most cerebrovascular disorders such as cerebral thrombosis and cerebral embolism, ischemic heart diseases such as myocardial infarction, and circulation disorders such as a peripheral circulation disorder are caused by a thrombus which is produced in a blood vessel and which occludes the blood vessel. Such a thrombus is produced mainly because platelets agglutinate in the earlier stage of the formation of the thrombus.

As compounds having a platelet agglutination inhibitory action, various 4-phenylphthalazine derivatives are conventionally known. For example, Japanese Patent Laid-Open Nos. 53659/1981, 53660/1981 and 48972/1982 disclose 1-anylino-4-phenylphthalazine derivatives, and Japanese Patent Laid-Open Nos. 218377/1985 and 243074/1985 disclose the compounds represented by the following general formulas (II) and (III), respectively, as compounds having a strong platelet agglutination inhibitory action in vitro:

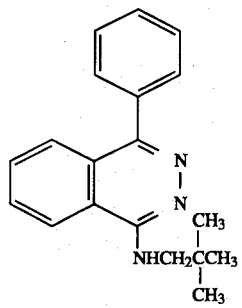

(II)

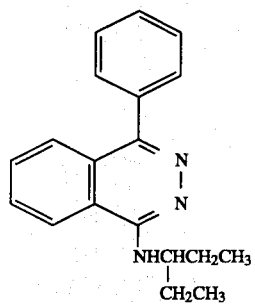

(III)

These compounds, however, show almost no platelet agglutination inhibitory action whey they are administered orally, or the platelet agglutination inhibitory action in vivo cannot be said to be satisfactory.

British Patent No. 1303016, *Journal of Medicinal Chemistry*, 12,555 (1969), etc. disclose 1-amino-4-phenylphthalazine derivatives represented by the following general formula (IV):

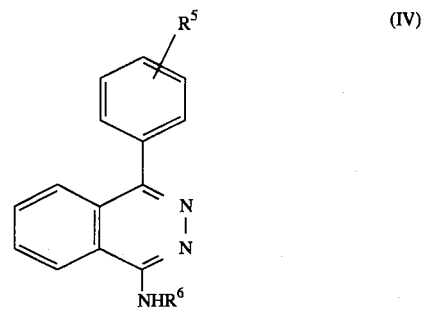

wherein $R^5$ represents a hydrogen atom or a chlorine atom, $R^6$ represents an alkyl group having 1 to 3 carbon atoms, —$(CH_2)_y N(CH_3)_2$, wherein y represents 2 or 3, a cyclohexyl group, or

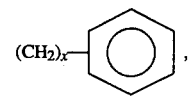

wherein x represents 1 or 2.

However, the compounds concretely disclosed have a restricted structure, and only an anti-inflammatory action and an anti-rheumatoid action are described as the pharmaceutical effects thereof.

As phthalazine derivatives having a non-substituted imidazole group at the fourth position, Japanese Patent Laid-Open Nos. 129180/1990, 129181/1990, 129182/1990 and 129183/1990 disclose compounds represented by the following general formulas (V) to (VIII), respectively:

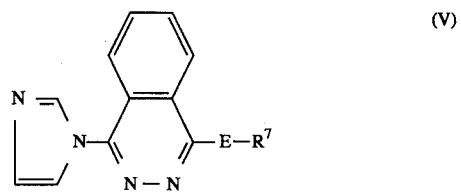

(V)

wherein E represents —NH—, —O— or —S—, and $R^7$ represents a straight-chain or branched-chain alkyl group having ! to 18 carbon atoms, a straight-chain or branched-chain alkyl group having 2 to 4 carbon atoms containing a hydroxyl group, an allyl group, a 3-methoxypropyl group, a tetrahydrofurfuryl group, a furfuryl group, a benzyl group which may be substituted by a chlorine atom or an alkyl group, or a phenyl group which may be substituted by a phenethyl group, a pyridylmethyl group or a chlorine atom, provided that when E is —NH—, $R^7$ is not a substituted or non-substituted phenyl group;

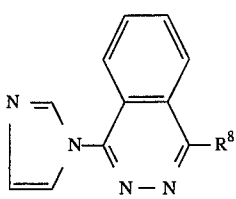

wherein R[8] represents a lower alkoxyphenyl group, an allyloxyphenyl group, a pyridylmethyloxyphenyl group, a furyl group which may have a substituent, a thienyl group which may have a substituent, or a naphthyl group which may have a substituent;

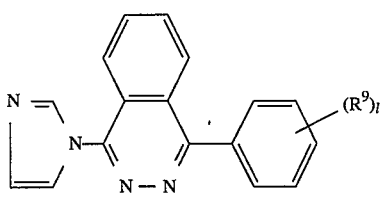

wherein R[9] which may be the same or different from each other represents a hydroxyl group, a lower alkyl group, a methoxy group, an acetylamino group, a halogen atom, a methylthio group or an ethoxycarbonylvinyl group, and l represents an integer of 0 to 3; and

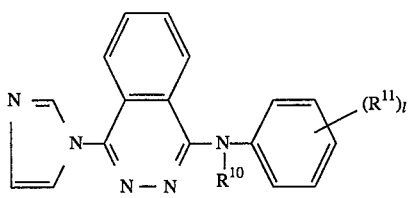

wherein R[10] represents a hydrogen atom, a lower alkyl group, R[11] which may be the same or different from each other represents a hydroxyl group, an alkyl group having 1 to 5 carbon atoms, a lower alkoxy group, an acylamino group, a halogen atom, a cyano group, a nitro group, an anmino group, a carboxyl group, a lower alkoxycarbonyl group, a lower alkylcarbonyl group or an alkylthio group, and l represents an integer of 0 to 3.

As a phthalazine derivative having a non-substituted pyridyl group at the fourth position, Japanese Patent Laid-Open No. 106873/1991 discloses a compound represented by the following general formulas (IX):

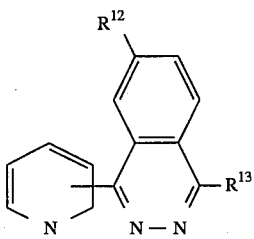

wherein R[12] represents a hydrogen atom or a methoxy group, and R[13] represents —NR[14]R[15], wherein R[14] represents an alkyl group, a phenyl group which may be substituted by a halogen atom or a cyano group, or a pyrimidinyl group which may have a substituent, and R[15] represents a hydrogen atom or a lower alkyl group, or R[14] and R[15] may combine to form a piperidino group, a piperazino group, a morpholino group or an imidazolyl group.

SUMMARY OF THE INVENTION

As a result of studies of pyridazine derivatives having excellent platelet agglutination inhibitory action, the present inventors have found that 3,6-disubstituted pyridazine derivatives satisfy the above-described requirements. The present invention has been achieved on the basis of this finding.

The present invention provides 3,6-disubstituted pyridazine derivatives represented by the following general formula (I), optical antipodes thereof and pharmaceutically acceptable acid-addition salts thereof:

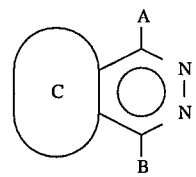

wherein A represents an alkyl group having 3 to 6 carbon atoms; a cycloalkyl group having 5 to 7 carbon atoms; a phenyl group, a thienyl group, a furyl group, a thiazolyl group, a phenoxy group, a phenylalkyl group having 7 to 9 carbon atoms, a phenylthio group, a nitrogen-containing saturated cyclic group, a pyridyl group or an imidazolyl group each of which may have at least one substituent selected from the group consisting of an alkyl group having 1 to 4 carbon atoms, an alkoxy group having 1 to 4 carbon atoms and a halogen atom; B represents —NH—D [wherein D represents

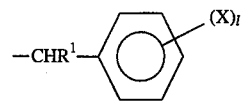

(wherein R[1] represents a hydrogen atom or an alkyl group having 1 to 4 carbon atoms, X independently represents a halogen atom, an alkyl group having 1 to 4 carbon atoms or an alkoxy group having 1 to 4 carbon atoms, and l represents an integer of 0 to 3),

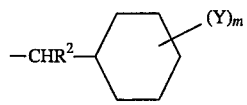

(wherein R[2] represents a hydrogen atom or an alkyl group having 1 to 4 carbon atoms, Y independently represents an alkyl group having 1 to 4 carbon atoms or an alkoxy group having 1 to 4 carbon atoms, or any given two Ys may combine to form an alkylene group having 1 to 3 carbon atoms which may be substituted by an alkyl group having 1 to 3 carbon atoms, and m represents an integer of 0 to 6);

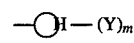

(wherein the ring H represents a cycloalkyl group having 5 to 7 carbon atoms, and Y and m are as defined above), —CHR[3]R[4] (wherein R[3] represents an alkyl group having 1 to 5 carbon atoms, and R[4] represents a cycloalkyl group having 5 to 8 carbon atoms or a thienyl group), or an alkyl group having 3 to 8 carbon atoms]; or

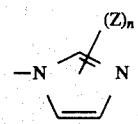

(wherein Z independently represents an alkyl group having 1 to 4 carbon atoms or a phenyl group, and n represents an integer of 0 to 2); and the ring C represents a benzene ring; a furan ring; or a thiophene ring which may be substituted by an alkyl group having 1 to 4 carbon atoms, provided that the following compounds (1) to (4) are excluded:

(1) compounds represented by the formula (I) wherein A represents a non-substituted imidazolyl group, the ring C represents a benzene ring, and B represents

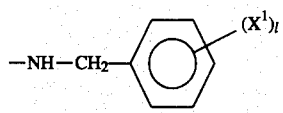

(wherein $X_1$ independently represents a halogen atom or an alkyl group having 1 to 4 carbon atoms, and l is as defined above), or an alkylamino group having 3 to 8 carbon atoms;

(2) compounds represented by the formula (I) wherein A represents a phenyl group which may have a substituent, the ring C represents a benzene ring, and B represents

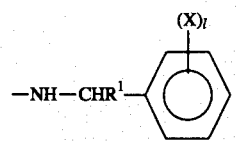

(wherein $R^1$, X and l are as defined above);

(3) compounds represented by the formula (I) wherein A represents a non-substituted phenyl group, the ring C represents a benzene ring, and B represents an alkylamino group having 3 to 8 carbon atoms; and (4) compounds represented by the formula (I) wherein A represents a pyridyl group, the ring C represents a benzene ring, and B represents an alkylamino group having 3 to 8 carbon atoms.

The present invention also provides a pharmaceutical composition containing, as an active ingredient, a 3,6-disubstituted pyridazine derivative of the above formula (I), an optical antipode thereof and a salt thereof.

The present invention also provides a process for the preparation of a 3,6-disubstituted pyridazine derivative of the above formula (I), an optical antipode thereof or a salt thereof.

DESCRIPTION OF THE PREFERRED EMBODIMENTS

Compounds according to the present invention are 3,6-disubstituted pyridazine derivatives represented by the following general formula (I), optical antipodes thereof and pharmaceutically acceptable acid-addition salts thereof:

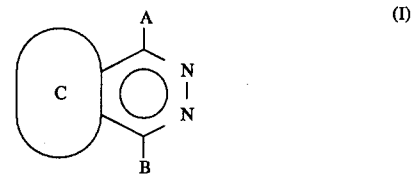

wherein A represents an alkyl group having 3 to 6 carbon atoms (e.g., propyl group and hexyl group); a cycloalkyl group having 5 to 7 carbon atoms (e.g., cyclopentyl group and cycloheptyl group); a phenyl group, a thienyl group (e.g., 2-thienyl group and 3-thienyl group), a furyl group (e.g., 2-furyl group and 3-furyl group), a thiazolyl group (e.g., 2-thiazolyl group), a phenoxy group, a phenylalkyl group having 7 to 9 carbon atoms (e.g., benzyl group and phenylpropyl group), a phenylthio group, a nitrogen-containing saturated cyclic group (e.g., pyrrolidino group, piperidino group and morpholino group), a pyridyl group (e.g., 2-pyridyl group and 3-pyridyl group), or an imidazolyl group (e.g., 1-imidazolyl group and 2-imidazolyl group) each of which may have at least one substituent selected from the group consisting of an alkyl group having 1 to 4 carbon atoms (e.g, methyl group and butyl group), an alkoxy group having 1 to 4 carbon atoms (e.g., methoxy group and butoxy group) and a halogen atom (e.g., fluorine atom, chlorine atom, bromine atom and iodine atom); B represents —NH—D [wherein D represents

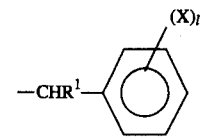

(wherein $R^1$ represents a hydrogen atom or an alkyl group having 1 to 4 carbon atoms (e.g., methyl group and butyl group), X independently represents a halogen atom (e.g., fluorine atom, chlorine atom, bromine atom and iodine atom), an alkyl group having 1 to 4 carbon atoms (e.g., methyl group and butyl group) or an alkoxy group having 1 to 4 carbon atoms (e.g., methoxy group and butoxy group), and l represents an integer of 0 to 3),

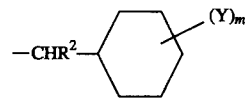

(wherein $R^2$ represents a hydrogen atom or an alkyl group having 1 to 4 carbon atoms (e.g., methyl group and butyl group), Y independently represents an alkyl group having 1 to 4 carbon atoms (e.g., methyl group, butyl group) or an alkoxy group having 1 to 4 carbon atoms (e.g., methoxy group and butoxy group), or any given two Ys may combine to form an alkylene group having 1 to 3 carbon atoms (e.g., methylene group and propylene group) which may be substituted by an alkyl group having 1 to 3 carbon atoms (e,g., methyl group and propyl group), and m represents an integer of 0 to 6), $$-\underset{}{\bigcirc}H-(Y)_m$$

(wherein the ring H represents a cycloalkyl group having 5 to 7 carbon atoms (e.g., cyclopentyl group and cycloheptyl group), and Y and m represent are as defined above), —CHR$^3$R$^4$ (wherein R$^3$ represents an alkyl group having 1 to 5 carbon atoms (e,g., methyl group, propyl group and pentyl group), and R$^4$ represents a cycloalkyl group having 5 to 8 carbon atoms (e,g., cyclopentyl group and cyclooctyl group) or a thienyl group (e.g., 2-thienyl group and 3-thienyl group)), or an alkyl group having 3 to 8 carbon atoms (e.g., propyl group, pentyl group and octyl group)]; or $$-N\underset{\diagdown\!=\!\diagup}{\overset{(Z)_n}{\diagup\!\!\!\!\diagdown}}N$$

(wherein Z independently represents an alkyl group having 1 to 4 carbon atoms (e.g., methyl group and butyl group) or a phenyl group, and n represents an integer of 0 to 2); and the ring C represents a benzene ring; a furan ring; or a thiophene ring which may be substituted by an alkyl group having 1 to 4 carbon atoms (e.g., methyl group and butyl group), provided that the following compounds (1) to (4) are excluded:

(1) compounds represented by the formula (I) wherein A is a non-substituted imidazolyl group, the ring C is a benzene ring, and B is $$-NH-CH_2-\underset{}{\bigcirc}-(X^1)_l$$

(wherein X$_1$ independently represents a halogen atom or an alkyl group having 1 to 4 carbon atoms, and l is as defined above) or an alkylamino group having 3 to 8 carbon atoms;

(2) compounds represented by the formula (I) wherein A is a phenyl group which may have a substituent, the ring C is a benzene ring, and B is $$-NH-CHR^1-\underset{}{\bigcirc}-(X)_l$$

(wherein R$^1$, X and l are as defined above);

(3) compounds represented by the formula (I) wherein A is a non-substituted phenyl group, the ring C is a benzene ring, and B is an alkylamino group having 3 to 8 carbon atoms; and (4) compounds represented by the formula (I) wherein A is a pyridyl group, the ring C is a benzene ring, and B is an alkylamino group having 3 to 8 carbon atoms.

Among these, examples of preferable compounds are:

(1) compounds represented by the formula (I) wherein A represents an alkyl group having 3 to 6 carbon atoms; a cycloalkyl group having 5 to 7 carbon atoms; a thienyl group, a furyl group, a thiazolyl group or a phenoxy group, a phenylalkyl group having 7 to 9 carbon atoms, a phenylthio group, a nitrogen-containing saturated cyclic group or an imidazolyl group, each of which may have at least one substituent selected from the group consisting of an alkyl group having 1 to 3 carbon atoms and a halogen atom; B represents —NH—D [wherein D represents $$-CHR^1-\underset{}{\bigcirc}-(X)_l$$

(wherein R$^1$ represents an alkyl group having 1 to 4 carbon atoms, and X and l represent the same as defined above, $$-CHR^2-\underset{}{\bigcirc}-(Y)_m$$

(wherein R$^2$, Y and m are as defined above), $$-\underset{}{\bigcirc}H-(Y)_m$$

(wherein the ring H, Y and m are as defined above), or an alkyl group having 3 to 8 carbon atoms]; or $$-N\underset{\diagdown\!=\!\diagup}{\overset{(Z)_n}{\diagup\!\!\!\!\diagdown}}N$$

(wherein Z and n are as defined above); and the ring C represents a benzene ring;

(2) compounds represented by the formula (I) wherein A represents a phenyl group which may have at least one substituent selected from the group consisting of an alkyl group having 1 to 4 carbon atoms, an alkoxy group having 1 to 4 carbon atoms and a halogen atom; B represents —NH—D [wherein D represents —CHR$^3$R$^4$ (wherein R$^3$ and R$^4$ are as defined above)]; and the ring C represents a benzene ring; and (3) compounds represented by the formula (I) wherein A represents an alkyl group having 3 to 6 carbon atoms; a cycloalkyl group having 5 to 7 carbon atoms; a phenyl group, a thienyl group or a pyridyl group each of which may have at least one substituent selected from the group consisting of an alkyl group having 1 to 3 carbon atoms and a halogen atom; B represents —NH—D [wherein D represents $$-CHR^1-\underset{}{\bigcirc}-(X)_l$$

(wherein R$^1$, X and l are as defined above);

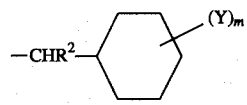

(wherein R², Y and m are as defined above); or

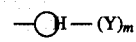

(wherein the ring H, Y and m are as defined above)]; and the ring C represents a furan ring or a thiophene ring each of which may be substituted by an alkyl group having 1 to 4 carbon atoms.

As examples of more preferable compounds will be cited compounds represented by the formula (I) wherein A represents a phenyl group which may be substituted by an alkyl group having 1 to 4 carbon atoms, a chlorine atom or an alkoxy group having 1 to 4 carbon atoms; an alkyl group having 3 to 6 carbon atoms; a cyclohexyl group; a thiazolyl group; a phenoxy group; a phenylthio group; a pyrrolidinyl group; a piperidyl group; a morpholinol group; a pyridyl group; a benzyl group which may be substituted by a halogen atom; or a thienyl group, a furyl group or an imidazolyl group each of which may be substituted by an alkyl group having 1 to 3 carbon atoms; B represents —NH—D [wherein D represents

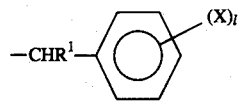

(wherein R¹ represents an alkyl group having 1 to 4 carbon atoms, and X represents a chlorine atom, an alkyl group having 1 to 4 carbon atoms or an alkoxy group having 1 to 4 carbon atoms, and l represents 0 or 1),

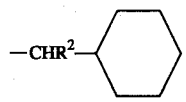

(wherein R² represents an alkyl group having 1 to 4 carbon atoms),

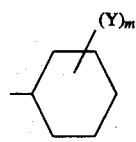

(wherein Y independently represents an alkyl group having 1 to 4 carbon atoms or any given two Ys may combine to form an alkylene group having 1 to 3 carbon atoms which may be substituted by an alkyl group having 1 to 3 carbon atoms, and m represent an integer of 0 to 6), —CHR³R⁴ (wherein R³ represents an alkyl group having 1 to 5 carbon atoms, and R⁴ represents a cyclohexyl group or a thienyl group), or an alkyl group having 3 to 8 carbon atoms]; or

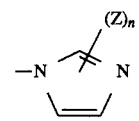

(wherein Z represents an alkyl group having 1 to 4 carbon atoms or a phenyl group, and n represents an integer of 0 or 1); and the ring C represents a benzene ring, or a furan ring or a thiophene ring each of which may be substituted by an alkyl group having 1 to 4 carbon atoms, provided that the following compounds (1) and (2) are excluded:

(1) compounds represented by the formula (I) wherein A is a phenyl group, B is an alkylamino group having 3 to 8 carbon atoms, and the ring C is a benzene ring; and (2) compounds represented by the formula (I) wherein A is a pyridyl group, B is an alkylamino group having 3 to 8 carbon atoms, and the ring C is a benzene ring.

Particularly preferably compounds are, for example, compounds represented by the formula (I) wherein A represents a phenyl group which may be substituted by an alkyl group having 1 to 4 carbon atoms, a chlorine atom or an alkoxy group having 1 to 4 carbon atoms; an alkyl group having 3 to 6 carbon atoms; a cyclohexyl group; a thiazolyl group; a pyrrolidinyl group; a piperidyl group; a morpholinol group; or a thienyl group, a furyl group or an imidazolyl group each of which may be substituted by an alkyl group having 1 to 3 carbon atoms; B represents —NH—D [wherein D represents

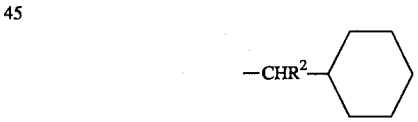

(wherein R¹ represents an alkyl group having 1 to 4 carbon atoms, and X represents a chlorine atom, an alkyl group having 1 to 4 carbon atoms or an alkoxy group having 1 to 4 carbon atoms, and l represents 0 or 1),

—CHR²—◯

(wherein R² represents an alkyl group having 1 to 4 carbon atoms),

(wherein Y independently represents an alkyl group having 1 to 4 carbon atoms or any given two Ys may combine to form an alkylene group having 1 to 3 carbon atoms which may be substituted by an alkyl group having 1 to 3 carbon atoms, and m represent an integer of 0 to 6), —CHR³R⁴ (wherein R³ represents an alkyl group having 1 to 5 carbon atoms, and R⁴ represents a cyclohexyl group or a thienyl group), or an alkyl group having 3 to 8 carbon atoms]; or

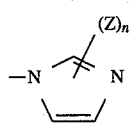

(wherein Z represents an alkyl group having 1 to 4 carbon atoms or a phenyl group, and n represents an integer of 0 or 1); and the ring C represents a benzene ring; or a furan ring or a thiophene ring each of which may be substituted by an alkyl group having 1 to 4 carbon atoms, provided that compounds represented by the formula (I) wherein A is a phenyl group, B is an alkylamino group having 3 to 8 carbon atoms, and the ring C is a benzene ring are excluded.

Examples of the most preferable compounds are compounds represented by the formula (I) wherein A represents a phenyl group; or a furyl group or a thienyl group each of which may be substituted by an alkyl group having 1 to 4 carbon atoms, B represents —NH—D [wherein D represents $$-CHR^2-\bigcirc$$

(wherein $R^2$ represents an alkyl group having 1 to 4 carbon atoms)], and the ring C represents a benzene ring, or a furan ring or a thiophene ring each of which may be substituted by an alkyl group having 1 to 4 carbon atoms.

Concrete examples of the compounds according to the present invention will be shown in Tables 1 to 5.

TABLE 1

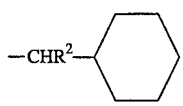

| Comp. No. | A | B |
|---|---|---|
| 1 | —⟨H⟩ | —NH—CH(CH₃)—C₆H₅ |
| 2 | —⟨H⟩ | —NH—CH(CH₂CH₃)—C₆H₅ |
| 3 | —⟨H⟩ | —NH—CH(CH₂CH₂CH₃)—C₆H₅ |
| 4 | —⟨H⟩ | —NH—CH(CH₂CH₂CH₂CH₃)—C₆H₅ |

TABLE 1-continued

| Comp. No. | A | B |
|---|---|---|
| 5 | —⟨H⟩ | —NH—CH(CH₃)—C₆H₄(o-CH₃) |
| 6 | —⟨H⟩ | —NH—CH(CH₃)—C₆H₄(m-CH₃) |
| 7 | —⟨H⟩ | —NH—CH(CH₃)—C₆H₄(p-CH₃) |
| 8 | —⟨H⟩ | —NH—CH(CH₃)—C₆H₄(p-C₂H₅) |
| 9 | —⟨H⟩ | —NH—CH(CH₃)—C₆H₄(p-C₃H₇(n)) |
| 10 | —⟨H⟩ | —NH—CH(CH₃)—C₆H₄(p-C₄H₉(n)) |
| 11 | —⟨H⟩ | —NH—CH(CH₃)—C₆H₄(o-OCH₃) |
| 12 | —⟨H⟩ | —NH—CH(CH₃)—C₆H₄(m-OCH₃) |
| 13 | —⟨H⟩ | —NH—CH(CH₃)—C₆H₄(p-OCH₃) |
| 14 | —⟨H⟩ | —NH—CH(CH₃)—C₆H₄(p-OC₂H₅) |
| 15 | —⟨H⟩ | —NH—CH(CH₃)—C₆H₄(p-OC₃H₇(n)) |
| 16 | —⟨H⟩ | —NH—CH(CH₃)—C₆H₄(p-OC₄H₉(n)) |

TABLE 1-continued

| # | R | R' |
|---|---|---|
| 17 | cyclohexyl-H | -NH-CH(CH₃)-(2-Cl-phenyl) |
| 18 | cyclohexyl-H | -NH-CH(CH₃)-(3-Cl-phenyl) |
| 19 | cyclohexyl-H | -NH-CH(CH₃)-(4-Cl-phenyl) |
| 20 | cyclohexyl-H | -NH-CH(CH₃)-(2-F-phenyl) |
| 21 | cyclohexyl-H | -NH-CH(CH₃)-(3-F-phenyl) |
| 22 | cyclohexyl-H | -NH-CH(CH₃)-(4-F-phenyl) |
| 23 | cyclohexyl-H | -NH-CH(CH₃)-cyclohexyl(H) |
| 24 | cyclohexyl-H | -NH-CH(CH₂CH₃)-cyclohexyl(H) |
| 25 | cyclohexyl-H | -NH-CH(CH₂CH₂CH₃)-cyclohexyl(H) |
| 26 | cyclohexyl-H | -NH-CH(CH₂CH₂CH₂CH₃)-cyclohexyl(H) |
| 27 | cyclohexyl-H | imidazol-1-yl |
| 28 | cyclohexyl-H | 2-methyl-imidazol-1-yl |
| 29 | cyclohexyl-H | 4-methyl-imidazol-1-yl |
| 30 | cyclohexyl-H | 4-ethyl-imidazol-1-yl (−C₂H₅) |
| 31 | cyclohexyl-H | 4-n-propyl-imidazol-1-yl (−C₃H₇(n)) |
| 32 | cyclohexyl-H | 4-n-butyl-imidazol-1-yl (−C₄H₉(n)) |
| 33 | cyclohexyl-H | 4-phenyl-imidazol-1-yl |
| 34 | cyclohexyl-H | -NH-cyclohexyl(H) |
| 35 | cyclohexyl-H | -NH-(2-CH₃-cyclohexyl)(H) |
| 36 | cyclohexyl-H | -NH-(3-CH₃-cyclohexyl)(H) |
| 37 | cyclohexyl-H | -NH-(4-CH₃-cyclohexyl)(H) |
| 38 | cyclohexyl-H | -NH-(2,3-diCH₃-cyclohexyl)(H) |
| 39 | cyclohexyl-H | -NH-(2,6-diCH₃-cyclohexyl)(H) |
| 40 | cyclohexyl-H | -NH-(3,3,5,5-tetraCH₃-cyclohexyl)(H) |

TABLE 1-continued

| # | R1 | R2 |
|---|---|---|
| 41 | —⬡H | —NH—⬡H—C₂H₅ |
| 42 | —⬡H | —NH—⬡H—C₃H₇(n) |
| 43 | —⬡H | —NH—⬡H—C₄H₉(n) |
| 44 | —⬡H | —NH—(bicyclic) |
| 45 | —⬡H | —NH—⬠H |
| 46 | —⬡H | |
| 47 | —⬡H | —NH—(CH₂)₂CH₃ |
| 48 | —⬡H | —NH—(CH₂)₃CH₃ |
| 49 | —⬡H | —NH—(CH₂)₄CH₃ |
| 50 | —⬡H | —NH—(CH₂)₅CH₃ |
| 51 | —⬡H | —NH—(CH₂)₆CH₃ |
| 52 | —⬡H | —NH—(CH₂)₇CH₃ |
| 53 | —⬡H | |
| 54 | —⬡H | |
| 55 | —⬡H | |
| 56 | —⬡H | |
| 57 | —⬡H | |
| 58 | —⬡H | |
| 59 | —⬡H | |
| 60 | —⬡H | |
| 61 | —⬡H | |
| 62 | —⬡H | |
| 63 | —⬡H | —NHC(CH₃)₃ |
| 64 | —⬡H | —NHCH₂C(CH₃)₃ |
| 65 | —⬡H | |
| 66 | —⬡H | |
| 67 | —(CH₂)₂CH₃ | —NH—CH(C₆H₅)CH₃ |
| 68 | —(CH₂)₂CH₃ | —NH—CH(C₆H₅)CH₂CH₃ |
| 69 | —(CH₂)₂CH₃ | —NH—CH(⬡H)CH₃ |

TABLE 1-continued

| | | |
|---|---|---|
| 70 | —(CH₂)₂CH₃ | —NH—CH(CH₂CH₃)(C₆H₁₁) |
| 71 | —(CH₂)₂CH₃ | imidazol-1-yl |
| 72 | —(CH₂)₂CH₃ | —NH—C₆H₁₁ |
| 73 | —(CH₂)₂CH₃ | |
| 74 | —(CH₂)₂CH₃ | —NH—CH₂C(CH₃)₃ |
| 75 | —CH(CH₃)₂ | —NH—CH(CH₃)(C₆H₅) |
| 76 | —CH(CH₃)₂ | —NH—CH(CH₂CH₃)(C₆H₅) |
| 77 | —CH(CH₃)₂ | —NH—CH(CH₃)(C₆H₁₁) |
| 78 | —CH(CH₃)₂ | —NH—CH(CH₂CH₃)(C₆H₁₁) |
| 79 | —CH(CH₃)₂ | imidazol-1-yl |
| 80 | —CH(CH₃)₂ | —NH—C₆H₁₁ |
| 81 | —CH(CH₃)₂ | |
| 82 | —CH(CH₃)₂ | —NH—CH₂C(CH₃)₃ |
| 83 | —CH(CH₃)₂ | —NH—CH(CH₃)(C₆H₅) |
| 84 | —CH(CH₃)₂ | —NH—CH(CH₂CH₃)(C₆H₅) |
| 85 | —(CH₂)₃CH₃ | —NH—CH(CH₃)(C₆H₁₁) |
| 86 | —(CH₂)₃CH₃ | —NH—CH(CH₂CH₃)(C₆H₁₁) |
| 87 | —(CH₂)₃CH₃ | imidazol-1-yl |
| 88 | —(CH₂)₃CH₃ | —NH—C₆H₁₁ |
| 89 | —(CH₂)₃CH₃ | |
| 90 | —(CH₂)₃CH₃ | —NH—CH₂C(CH₃)₃ |
| 91 | —C(CH₃)₃ | —NH—CH(CH₃)(C₆H₅) |
| 92 | —C(CH₃)₃ | —NH—CH(CH₂CH₃)(C₆H₅) |
| 93 | —C(CH₃)₃ | —NH—CH(CH₃)(C₆H₁₁) |
| 94 | —C(CH₃)₃ | —NH—CH(CH₂CH₃)(C₆H₁₁) |
| 95 | —C(CH₃)₃ | imidazol-1-yl |
| 96 | —C(CH₃)₃ | —NH—C₆H₁₁ |
| 97 | —C(CH₃)₃ | |
| 98 | —C(CH₃)₃ | —NH—CH₂C(CH₃)₃ |
| 99 | —(CH₂)₄CH₃ | —NH—CH(CH₃)(C₆H₅) |
| 100 | —(CH₂)₄CH₃ | —NH—CH(CH₂CH₃)(C₆H₅) |
| 101 | —(CH₂)₄CH₃ | —NH—CH(CH₃)(C₆H₁₁) |

TABLE 1-continued

| # | R | R' |
|---|---|---|
| 102 | —(CH₂)₄CH₃ | —NH—CH(CH₂CH₃)(cyclohexyl), H |
| 103 | —(CH₂)₄CH₃ | imidazolyl (N–CH=N–CH=CH–) |
| 104 | —(CH₂)₄CH₃ | —NH—(cyclohexyl), H |
| 105 | —(CH₂)₄CH₃ | |
| 106 | —(CH₂)₄CH₃ | —NH—CH₂C(CH₃)₃ |
| 107 | —(CH₂)₅CH₃ | —NH—CH(CH₃)(phenyl) |
| 108 | —(CH₂)₅CH₃ | —NH—CH(CH₂CH₃)(phenyl) |
| 109 | —(CH₂)₅CH₃ | —NH—CH(CH₃)(cyclohexyl), H |
| 110 | —(CH₂)₅CH₃ | —NH—CH(CH₂CH₃)(cyclohexyl), H |
| 111 | —(CH₂)₅CH₃ | imidazolyl |
| 112 | —(CH₂)₅CH₃ | —NH—(cyclohexyl), H |
| 113 | —(CH₂)₅CH₃ | |
| 114 | —(CH₂)₅CH₃ | —NH—CH₂C(CH₃)₃ |
| 115 | | —NH—CH(CH₃)(phenyl) |
| 116 | | —NH—CH(CH₂CH₃)(phenyl) |
| 117 | | —NH—CH(CH₂CH₂CH₃)(phenyl) |
| 118 | | —NH—CH(CH₂CH₂CH₂CH₃)(phenyl) |
| 119 | | —NH—CH(CH₃)(2,6-dimethylphenyl) |
| 120 | | —NH—CH(CH₃)(3,5-dimethylphenyl) |
| 121 | | —NH—CH(CH₃)(4-methylphenyl) |
| 122 | | —NH—CH(CH₃)(4-ethylphenyl) |
| 123 | | —NH—CH(CH₃)(4-n-propylphenyl) |
| 124 | | —NH—CH(CH₃)(4-n-butylphenyl) |
| 125 | | —NH—CH(CH₃)(2-methoxyphenyl) |
| 126 | | —NH—CH(CH₃)(3-methoxyphenyl) |
| 127 | | —NH—CH(CH₃)(4-methoxyphenyl) |
| 128 | | —NH—CH(CH₃)(4-ethoxyphenyl) |
| 129 | | —NH—CH(CH₃)(4-n-propoxyphenyl) |

TABLE 1-continued
| No. | Structure |
|---|---|
| 130 | 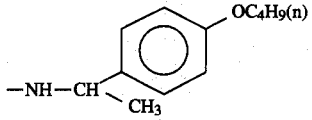 |
| 131 | 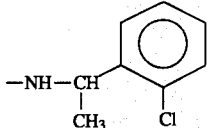 |
| 132 | 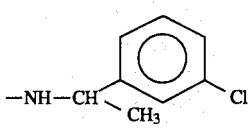 |
| 133 | 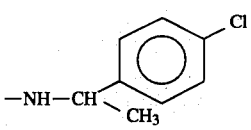 |
| 134 | 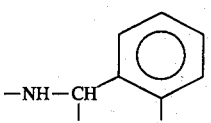 |
| 135 | 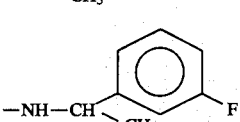 |
| 136 | 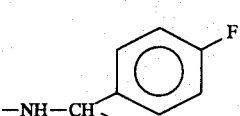 |
| 137 | 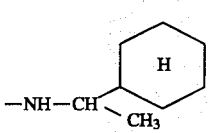 |
| 138 | 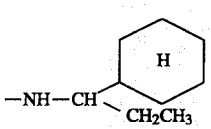 |
| 139 | 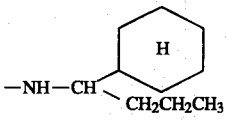 |
| 140 | 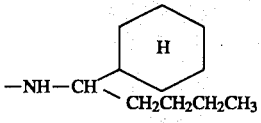 |
| 141 | 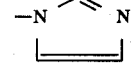 |
| 142 | 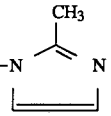 |
| 143 | 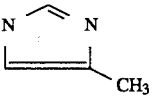 |
| 144 | 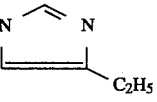 |
| 145 | 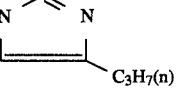 |
| 146 | 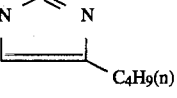 |
| 147 | 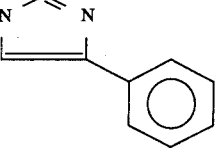 |
| 148 | 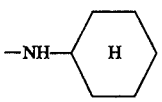 |
| 149 | 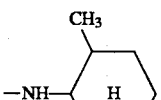 |
| 150 | 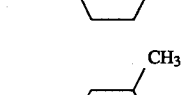 |
| 151 | 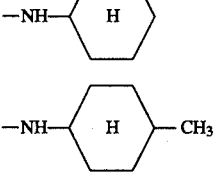 |
| 152 | 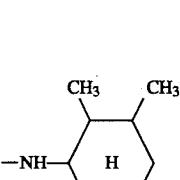 |
| 153 | 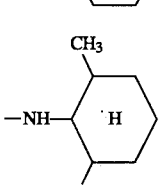 |

-continued
| | | | | |
|---|---|---|---|---|
| 154 | 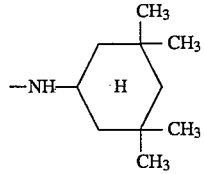 | | 181 |  |
| 155 | 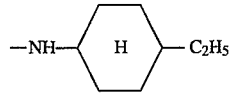 | | 182 | 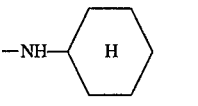 |
| 156 |  | | 183 |  |
| 157 | 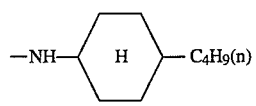 | | 184 |  |
| 158 | 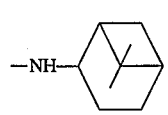 | | 185 |  |
| 159 | 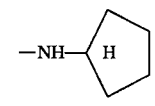 | | 186 | 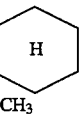 |
| 160 | | | 187 | |
| 161 | —NH—(CH$_2$)$_2$CH$_3$ | | 188 | —NH—CH$_2$C(CH$_3$)$_3$ |
| 162 | —NH—(CH$_2$)$_3$CH$_3$ | | 189 | 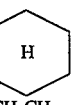 |
| 163 | —NH—(CH$_2$)$_4$CH$_3$ | | 190 |  |
| 164 | —NH—(CH$_2$)$_5$CH$_3$ | | 191 |  |
| 165 | —NH—(CH$_2$)$_6$CH$_3$ | | 192 |  |
| 166 | —NH—(CH$_2$)$_7$CH$_3$ | | 193 | 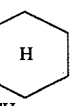 |
| 167 | | | 194 |  |
| 168 | | | 195 | |
| 169 | | | 196 | —NH—CH$_2$C(CH$_3$)$_3$ |
| 170 | | | | |
| 171 | | | | |
| 172 | | | | |
| 173 | | | | |
| 174 | | | | |
| 175 | | | | |
| 176 | | | | |
| 177 | —NHC(CH$_3$)$_3$ | | | |
| 178 | —NHCH$_2$C(CH$_3$)$_3$ | | | |
| 179 | | | | |
| 180 | | | | |

| No. | Structure |
|---|---|
| 197 | —NH—CH(CH₃)(C₆H₅) |
| 198 | —NH—CH(CH₂CH₃)(C₆H₅) |
| 199 | —NH—CH(CH₃)(C₆H₁₁) |
| 200 | —NH—CH(CH₂CH₃)(C₆H₁₁) |
| 201 | imidazol-1-yl |
| 202 | —NH—C₆H₁₁ |
| 203, 204 | —NH—CH₂C(CH₃)₃ |
| 205 | —NH—CH(CH₃)(C₆H₁₁) |
| 206 | —NH—CH(CH₃)(C₆H₁₁) |
| 207 | —NH—CH(CH₃)(C₆H₅) |
| 208 | —NH—CH(CH₂CH₃)(C₆H₅) |
| 209 | —NH—CH(CH₃)(C₆H₁₁) |
| 210 | —NH—CH(CH₂CH₃)(C₆H₁₁) |
| 211 | imidazol-1-yl |
| 212 | —NH—C₆H₁₁ |
| 213, 214 | —NH—CH₂C(CH₃)₃ |
| 215 | —NH—CH(CH₃)(C₆H₅) |
| 216 | —NH—CH(CH₂CH₃)(C₆H₅) |
| 217 | —NH—CH(CH₂CH₂CH₃)(C₆H₅) |
| 218 | —NH—CH(CH₂CH₂CH₂CH₃)(C₆H₅) |
| 219 | —NH—CH(CH₃)(2-CH₃-C₆H₄) |
| 220 | —NH—CH(CH₃)(3-CH₃-C₆H₄) |
| 221 | —NH—CH(CH₃)(4-CH₃-C₆H₄) |
| 222 | —NH—CH(CH₃)(4-C₂H₅-C₆H₄) |
| 223 | —NH—CH(CH₃)(4-n-C₃H₇-C₆H₄) |
| 224 | —NH—CH(CH₃)(4-n-C₄H₉-C₆H₄) |
| 225 | —NH—CH(CH₃)(2-OCH₃-C₆H₄) |

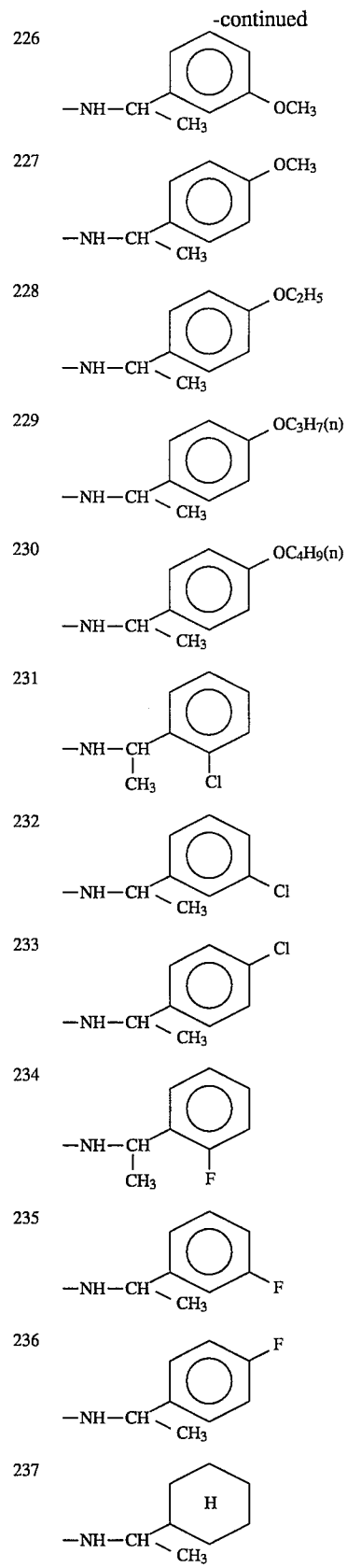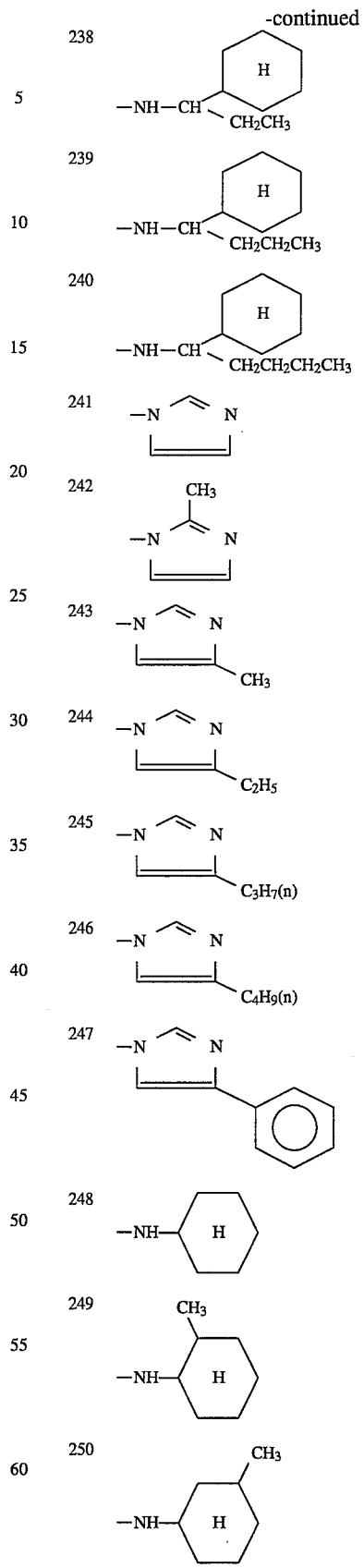

-continued
251 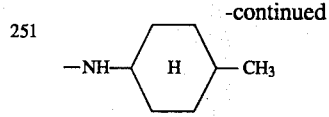
252 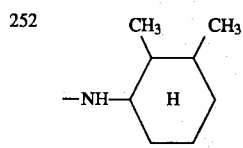
253 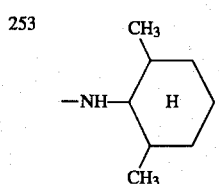
254 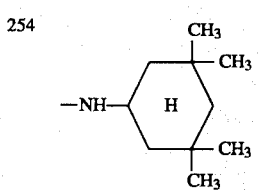
255 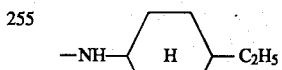
256 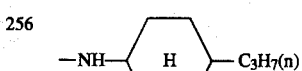
257 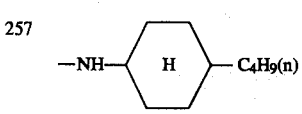
258 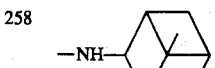
259 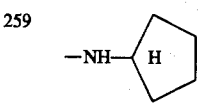
260
261 —NH—(CH$_2$)$_2$CH$_3$
262 —NH—(CH$_2$)$_3$CH$_3$
263 —NH—(CH$_2$)$_4$CH$_3$
264 —NH—(CH$_2$)$_5$CH$_3$
265 —NH—(CH$_2$)$_6$CH$_3$
266 —NH—(CH$_2$)$_7$CH$_3$
267
268
269
270
271
-continued
272
273
274
275
276
277 —NHC(CH$_3$)$_3$
278 —NHCH$_2$C(CH$_3$)$_3$
279
280
281 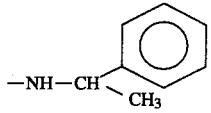
282 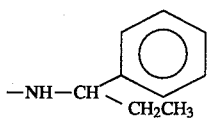
283 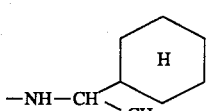
284 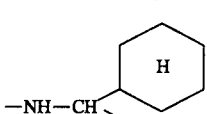
285 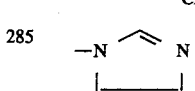
286 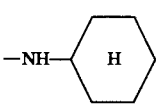
287
288 —NH—CH$_2$C(CH$_3$)$_3$
289 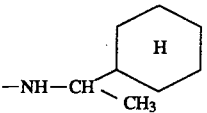
290 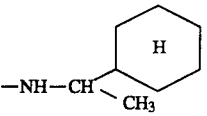
291 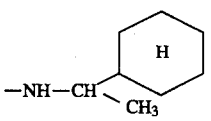
292 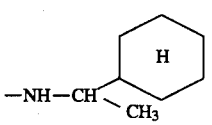

-continued

293 —NH—CH(CH₃)(cyclohexyl)

294 —NH—CH(CH₂CH₃)(cyclohexyl)

295 —NH—CH(CH₃)(phenyl)

296 —NH—CH(CH₂CH₃)(phenyl)

297 —N(imidazole)

298 —NH—(cyclohexyl)

299

300 —NH—CH₂C(CH₃)₃

301 —NH—CH(CH₃)(phenyl)

302 —NH—CH(CH₂CH₃)(phenyl)

303 —NH—CH(CH₃)(cyclohexyl)

304 —NH—CH(CH₂CH₃)(cyclohexyl)

305 —N(imidazole)

306 —NH—(cyclohexyl)

307

308 —NH—CH₂C(CH₃)₃

309 —NH—CH(CH₃)(cyclohexyl)

310 —NH—CH(CH₃)(cyclohexyl)

311 —NH—CH(CH₃)(cyclohexyl)

312 —NH—CH(CH₃)(cyclohexyl)

313 —NH—CH(CH₃)(cyclohexyl)

314 —NH—CH(CH₃)(cyclohexyl)

315 —NH—CH(CH₃)(cyclohexyl)

316 —NH—CH(CH₃)(phenyl)

317 —NH—CH(CH₂CH₃)(phenyl)

318 —NH—CH(CH₃)(cyclohexyl)

319 —NH—CH(CH₂CH₃)(cyclohexyl)

320 —N(imidazole)

321 —NH—(cyclohexyl)

322

323 —NH—CH₂C(CH₃)₃

-continued
324 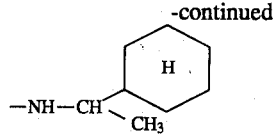
325 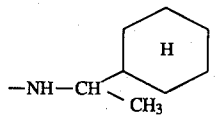
326 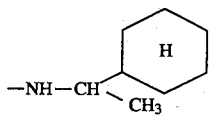
327 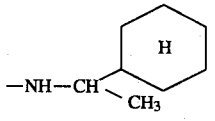
328 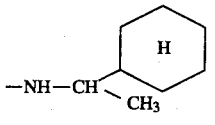
329 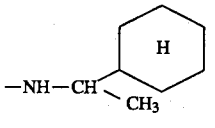
330 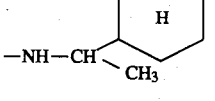
331 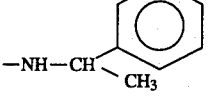
332 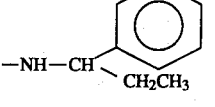
333 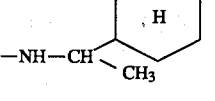
334 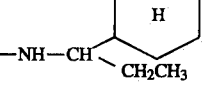
335 
336 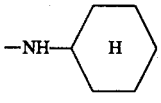
337
338 —NH—CH$_2$C(CH$_3$)$_3$
-continued
339 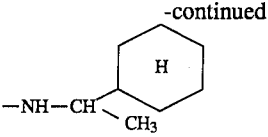
340 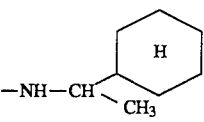
341 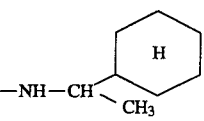
342 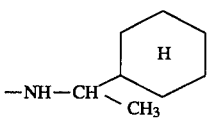
343 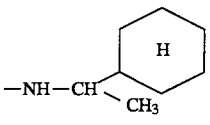
344 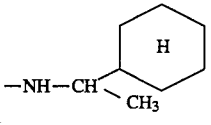
345 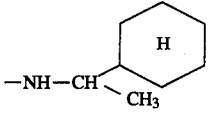
346 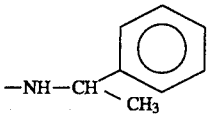
347 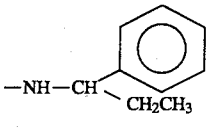
348 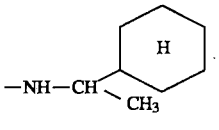
349 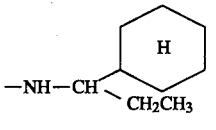
350 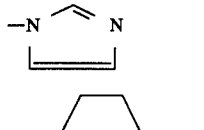
351 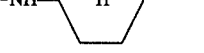
352
353 —NH—CH$_2$C(CH$_3$)$_3$

| No. | Structure |
|---|---|
| 354 | —NH—CH(CH₃)(C₆H₅) |
| 355 | —NH—CH(CH₂CH₃)(C₆H₅) |
| 356 | —NH—CH(CH₃)(C₆H₁₁) |
| 357 | —NH—CH(CH₂CH₃)(C₆H₁₁) |
| 358 | imidazol-1-yl |
| 359 | —NH—C₆H₁₁ |
| 360 | |
| 361 | —NH—CH₂C(CH₃)₃ |
| 362 | —NH—CH(CH₃)(C₆H₅) |
| 363 | —NH—CH(CH₂CH₃)(C₆H₅) |
| 364 | —NH—CH(CH₃)(C₆H₁₁) |
| 365 | —NH—CH(CH₂CH₃)(C₆H₁₁) |
| 366 | imidazol-1-yl |
| 367 | —NH—C₆H₁₁ |
| 368 | |
| 369 | —NH—CH₂C(CH₃)₃ |
| 370 | —NH—CH(CH₃)(C₆H₅) |
| 371 | —NH—CH(CH₂CH₃)(C₆H₅) |
| 372 | —NH—CH(CH₂CH₂CH₃)(C₆H₅) |
| 373 | —NH—CH(CH₂CH₂CH₂CH₃)(C₆H₅) |
| 374 | —NH—CH(CH₃)(2-CH₃-C₆H₄) |
| 375 | —NH—CH(CH₃)(3-CH₃-C₆H₄) |
| 376 | —NH—CH(CH₃)(4-CH₃-C₆H₄) |
| 377 | —NH—CH(CH₃)(4-C₂H₅-C₆H₄) |
| 378 | —NH—CH(CH₃)(4-n-C₃H₇-C₆H₄) |
| 379 | —NH—CH(CH₃)(4-n-C₄H₉-C₆H₄) |
| 380 | —NH—CH(CH₃)(2-OCH₃-C₆H₄) |

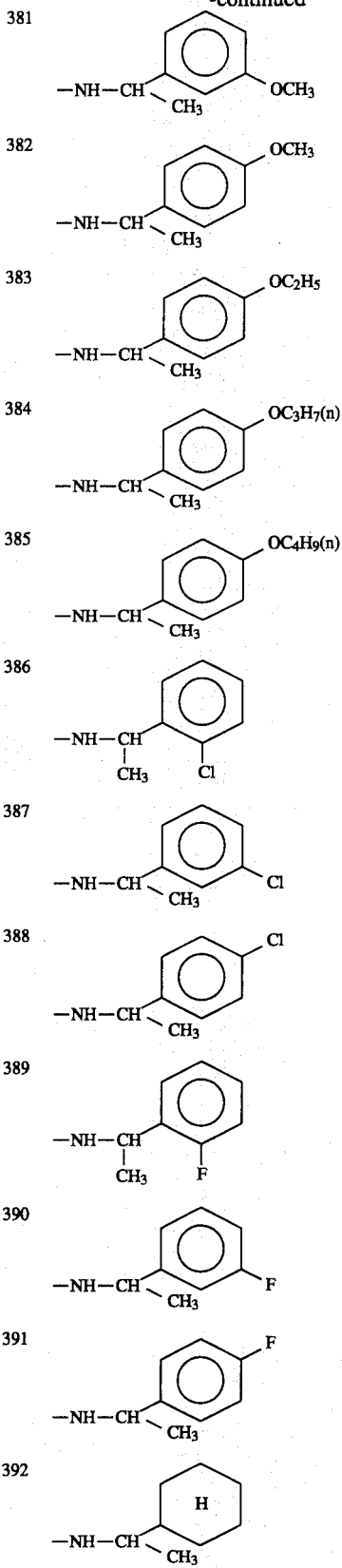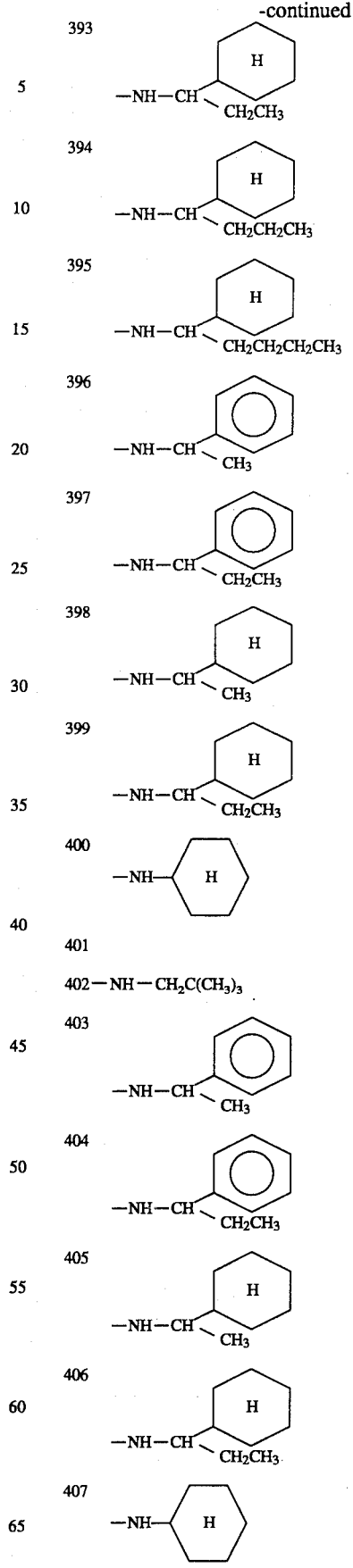

-continued
408
409 —NH—CH₂C(CH₃)₃
410 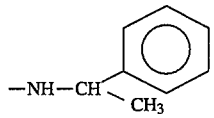
411 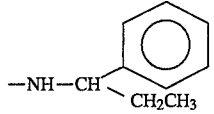
412 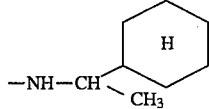
413 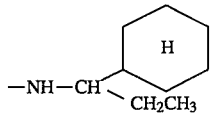
414 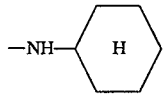
415
416 —NH—CH₂C(CH₃)₃
417 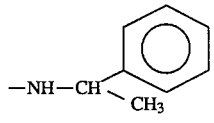
418 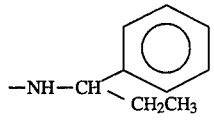
419 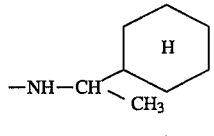
420 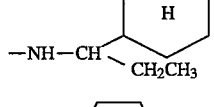
421 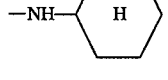
422
423 —NH—CH₂C(CH₃)₃
424 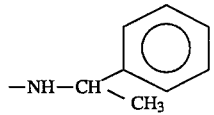
425 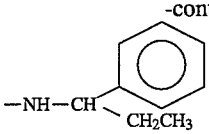
426 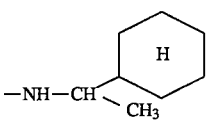
427 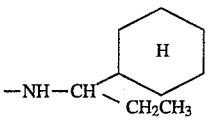
428 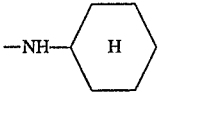
429
430 —NH—CH₂C(CH₃)₃
431 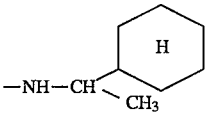
432 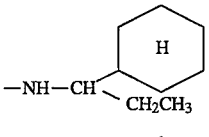
433 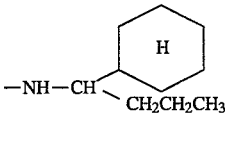
434
435 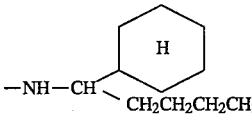
436
437
438
439
440
441
442
443 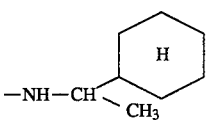
444 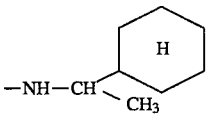

-continued

| | |
|---|---|
| 445 | —NH—CH(H)(CH₃)-cyclohexyl |
| 446 | —NH—CH(H)(CH₃)-cyclohexyl |
| 447 | —NH—CH(H)(CH₃)-cyclohexyl |
| 448 | —NH—CH(H)(CH₃)-cyclohexyl |
| 449 | —NH—CH(H)(CH₃)-cyclohexyl |
| 450 | —NH—CH(H)(CH₃)-cyclohexyl |
| 451 | —NH—CH(H)(CH₃)-cyclohexyl |
| 452 | —NH—CH(H)(CH₃)-cyclohexyl |
| 453 | —NH—CH(H)(CH₃)-cyclohexyl |
| 454 | —NH—CH(H)(CH₃)-cyclohexyl |
| 455 | —NH—CH(H)(CH₃)-cyclohexyl |
| 456 | —NH—CH(H)(CH₃)-cyclohexyl |
| 457 | —NH—CH(H)(CH₃)-cyclohexyl |
| 458 | —NH—CH(H)(CH₃)-cyclohexyl |
| 459 | —NH—CH(H)(CH₃)-cyclohexyl |
| 460 | —NH—CH(H)(CH₃)-cyclohexyl |
| 461 | —NH—CH(H)(CH₃)-cyclohexyl |
| 462 | —NH—CH(H)(CH₃)-cyclohexyl |
| 463 | —NH—CH(H)(CH₃)-cyclohexyl |
| 464 | —NH—CH(H)(CH₃)-cyclohexyl |
| 465 | —NH—CH(H)(CH₃)-cyclohexyl |
| 466 | —NH—CH(H)(CH₃)-cyclohexyl |
| 467 | —NH—CH(H)(CH₃)-cyclohexyl |
| 468 | —NH—CH(H)(CH₃)-cyclohexyl |
| 469 | —NH—CH(H)(CH₃)-cyclohexyl |
| 470 | —NH—CH(H)(CH₃)-cyclohexyl |

TABLE 2

| Comp. No. | A | B |
|---|---|---|
| 513 | phenyl | —NH—CH(CH₃)(phenyl) |
| 514 | phenyl | —NH—CH(CH₂CH₃)(phenyl) |
| 515 | phenyl | —NH—CH(CH₃)(2-chlorophenyl) |

TABLE 2-continued

[Structure with S, A, N-N, B on thieno-pyridazine scaffold]

| Comp. No. | A | B |
|---|---|---|
| 516 | phenyl | -NH-CH(CH₃)-(3-methylphenyl) |
| 517 | phenyl | -NH-CH(CH₃)-(2-methoxyphenyl) |
| 518 | phenyl | -NH-CH(CH₃)-cyclohexyl (R) |
| 519 | phenyl | -NH-CH(CH₂CH₃)-cyclohexyl |
| 520 | phenyl | -NH-CH(CH₂CH₂CH₃)-cyclohexyl |
| 521 | 3-chlorophenyl | -NH-CH(CH₃)-phenyl |
| 522 | 3-methylphenyl | -NH-CH(CH₃)-phenyl |
| 523 | 2-thienyl | -NH-CH(CH₃)-phenyl |
| 524 | phenyl | -NH-cyclohexyl |

TABLE 2-continued

[Structure with S, A, N-N, B on thieno-pyridazine scaffold]

| Comp. No. | A | B |
|---|---|---|
| 525 | phenyl | -NH-C(CH₃)₃ |

TABLE 3

[Structure with A, N-N, S, B on thieno-pyridazine scaffold (S at different position)]

| Comp. No. | A | B |
|---|---|---|
| 526 | phenyl | -NH-CH(CH₃)-phenyl |
| 527 | phenyl | -NH-CH(CH₃)-phenyl |
| 528 | phenyl | -NH-CH(CH₂CH₃)-phenyl |
| 529 | phenyl | -NH-CH(CH₂CH₂CH₂CH₃)-phenyl |
| 530 | phenyl | -NH-CH(CH₃)-(2-chlorophenyl) |

TABLE 3-continued
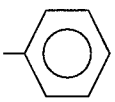
| Comp. No. | A | B |
|---|---|---|
| 531 | 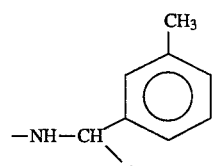 | 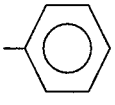 |
| 532 | 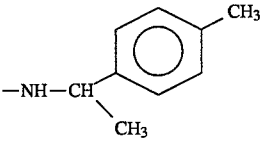 | 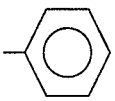 |
| 533 | 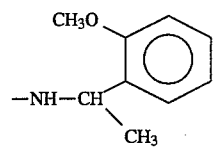 | 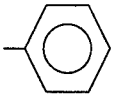 |
| 534 | 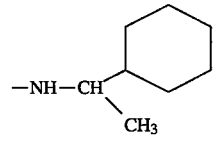 | 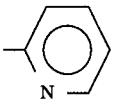 |
| 535 | 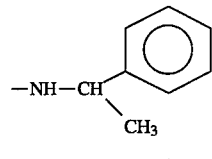 | 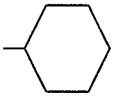 |
| 536 | 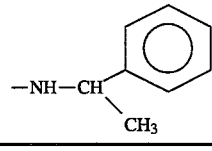 | 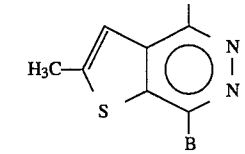 |
TABLE 4
| Comp. No. | A | B |
|---|---|---|
| 537 | 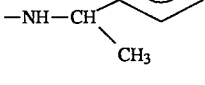 | 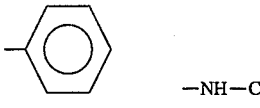 |
| 538 | 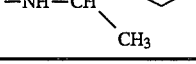 | 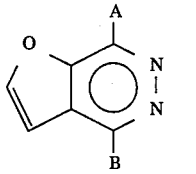 |
TABLE 5
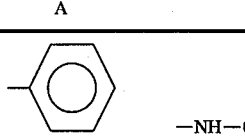
| Comp. No. | A | B |
|---|---|---|
| 539 | 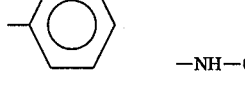 | 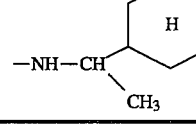 |
A process for preparing a compound according to the present invention will now be explained. A compound according to the present invention can be synthesized by a given method which meets the object of the present invention including the following methods.
(i) When the Ring C Represents a Benzene Ring

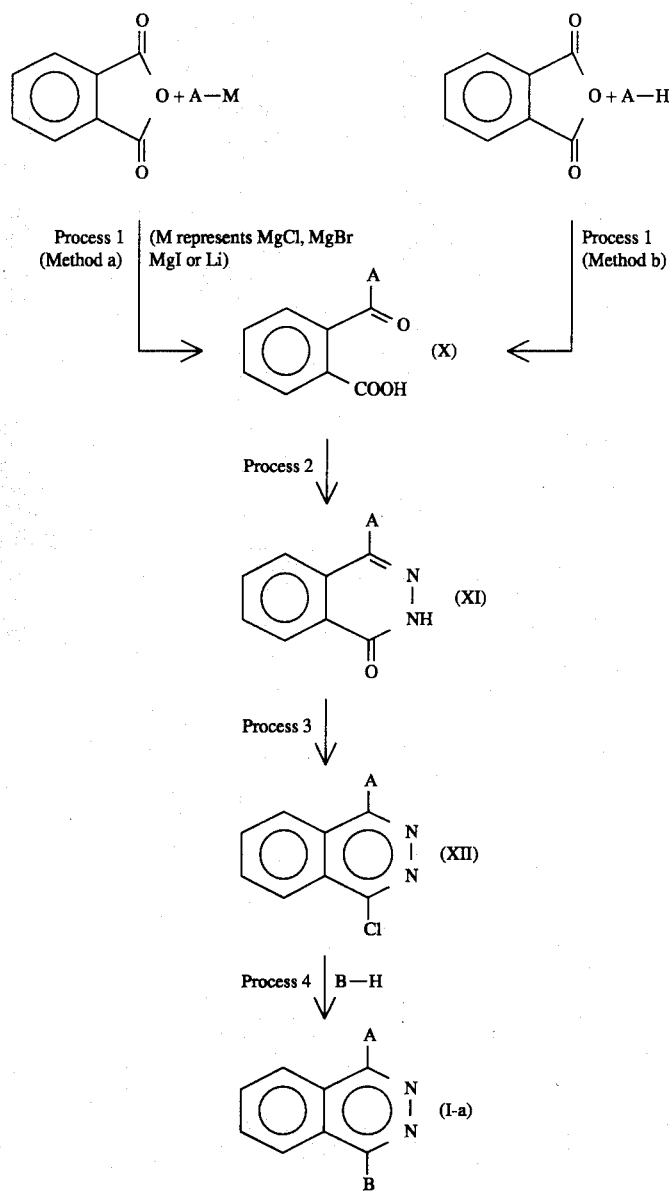

(A and B are as defined above)

The process 1 is a process for preparing a compound (X). The compound (X) can be prepared either by a method a or a method b. The method a is a method of preparing the compound (X) by reacting phthalic anhydride with Grignard reagent or lithium reagent. In the case of using a solvent, ether, tetrahydrofuran, dioxane, benzene, toluene, methylene chloride, dichloroethane, dimethyl formamide, N-methylpyrrolidone, hexamethylphosphoroamide or the like is used either singly or in the form of a mixture. The reaction temperature is −78° to 100° C., preferably −78° to 30° C., and the reaction time is 10 minutes to 24 hours.

The method b is a method of preparing the compound (X) by a Friedel-Crafts reaction between phthalic anhydride and a compound represented by the formula A—H, wherein A is as defined above. In the case of using a catalyst, aluminum chloride, titanium tetrachloride, tin chloride, boron trifluoride etherate or the like is used. In the case of using a solvent, methylene chloride, dichloroethane, nitrobenzene, carbon disulfide or the like is used. The reaction temperature is −78° to 200° C., preferably −50° to 100° C., and the reaction time is 10 minutes to 24 hours The process 2 is a process for preparing a compound (XI). By reacting the compound (X) and hydrazine or hydrazine hydrate, the compound (XI) is prepared. In the case of using a solvent, water, methanol, ethanol, benzene, toluene or the like is used. The reaction temperature is 0° to 150° C., preferably 20° to 100° C.

The process 3 is a process for preparing a compound (XII) by a chlorination of the compound (XI) without a solvent or in a solvent such as benzene, toluene, chloroform and dichloroethane. As a chlorinating agent, thionyl chloride, phosphorus oxychloride, phosphorus trichloride, phosphorus pentachloride or the like is used.

The process 4 is a process for preparing a compound (I -a) according to the present invention from the compound (XII). The compound (XII) is reacted with a compound represented by the formula B—H, wherein B represents the same as defined above. Examples of solvents used are ethers such as tetrahydrofuran and dioxane; hydrocarbon halides such as chloroform and dichloroethane; aromatic hydrocarbons such as benzene, toluene, xylene and chlorobenzene; amides such as dimethylformamide and N-methylpyrrolidone; and dimethylsulfoxide. The amount of solvent used is 0.1 to 100 by weight ratio based on the compound (XII). In the case of using a catalyst, an organic base such as triethylamine, disopropylethylamine, pyridine and N,N-dimethylanyline, or an inorganic base such as NaOH, KOH, NaHCO₃, Na₂CO₃, KHCO₃ and K₂CO₃ is used. The amount of catalyst used is 0.5 to 30, preferably 1 to 10 by weight ratio based on the compound (XII). The reaction temperature is 0° to 300° C., preferably 20° to 150° C., and the reaction time is 10 minutes to 24 hours.

(ii) When the Ring C Represents a Thiophene Ring Which May Be Substituted by an Alkyl Group Having 1 to 4 Carbon Atoms

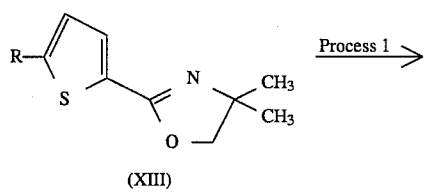

(XIII)

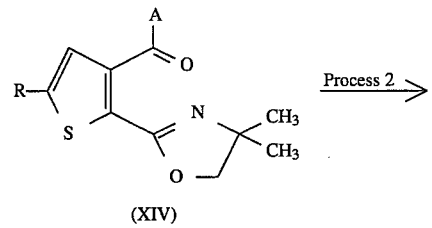

(XIV)

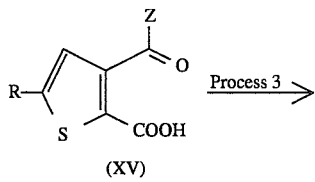

(XV)

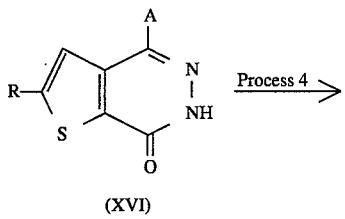

(XVI)

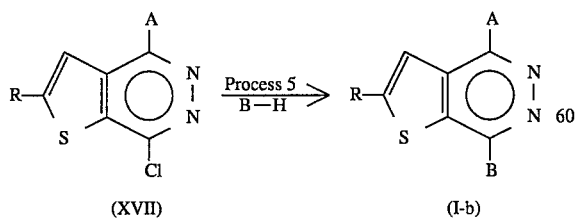

(XVII)  (I-b)

wherein A and B are as defined above and R represents an alkyl group having 1 to 4 carbon atoms.

The process 1 is a process for introducing

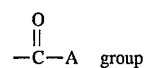

into the ortho position of a compound (XIII) so as to prepare a compound (XIV). A base such as butyl lithium is brought into reaction with the compound (XIII) so as to produce an ortho-lithiated compound. A compound represented by the general formula A—COR' (wherein A is as defined above, and R' represents a halogen atom, an alkoxy group, an imidazolyl group or a cyano group) is then reacted with the thus-produced ortho-lithiated compound, thereby preparing the compound (XIV). In the case of using a solvent, ether, tetrahydrofuran, etc. are used either singly or in the form of a mixture.

The process 2 is a process for cleaving the oxazoline ring of the compound (XIV) so as to prepare a compound (XV). The reaction is carried out in the presence of an acid such as hydrochloric acid, sulfuric acid, mesylic acid and tosylic acid. As a solvent, water, dioxane, tetrahydrofuran, ethanol, methanol, etc. are used either singly or in the form of a mixture.

The processes 3, 4 and 5 correspond to the processes 2, 3 and 4, respectively, in (i) when the ring C represents a benzene ring.

(iii) When the Ring C Represents a Furan Ring Which May Be Substituted By an Alkyl Group Having 1 to 4 Carbon Atoms

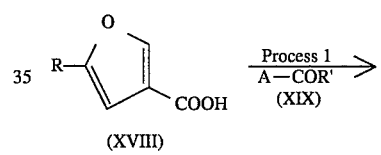

(XVIII)

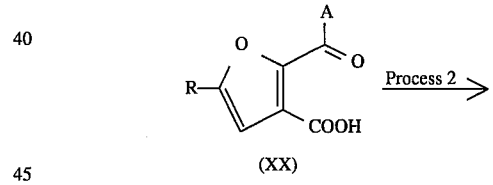

(XX)

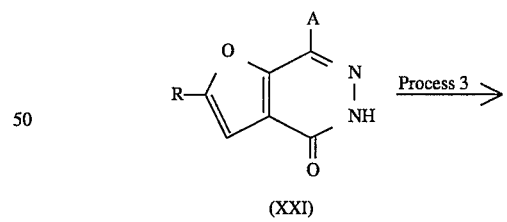

(XXI)

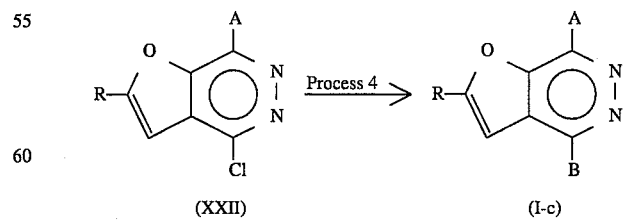

(XXII)  (I-c)

wherein A and B are as defined above and R represents an alkyl group having 1 to 4 carbon atoms.

The process 1 is a process for introducing A—C=O group into the second position of a compound (XVIII) so as to prepare a compound (XX). The reaction is carried out by bringing the dilithiated compound of the compound (XVIII) which is produced by a base into reaction with a compound represented by the general formula A—COR' (wherein A is as defined above, and R' represents a halogen atom, an alkoxy group, an aryloxy group, an imidazolyl group or a cyano group). At this time, n-butyllithium, s-butyllithium, LDA, LHMDS, etc. are usable as a base. The amount of base used is 1 to 10, preferably 2 to 4 by molar ratio. As a solvent, tetrahydrofuran, diethyl ether, diisopropyl ether, hexane, heptane, etc. are used either singly or in the form of a mixture.

The processes 2, 3, and 4 correspond to the processes 2, 3 and 4, respectively, in (i) when the ring C represents a benzene ring.

The salts of the compound represented by the general formula (I) are preferably physiologically tolerable salts. They are, for example, the salts of inorganic acids such as hydrochlorides, hydrobromides, hydroiodides, sulfides and phosphates, and the salts of organic acids such as methane sulfonates, p-toluene sulfonates, benzene sulfonates, camphor sulfonates, acetates, benzoates, malates, lactates, glycolates, glucronates, maleates, fumarates, oxalates, ascorbates, citrates, salicylates, nicotinates and tartrates. Since some compounds represented by the general formula (I) and some salts thereof exist in the form of a hydrate or a solvate, the compounds of the present invention include the hydrates and solvates thereof.

When a compound of the present invention is orally administered to an adult as a medicine, it is preferable that a dose of 1 to 100 mg is administered 1 to 3 times a day. In the case of using a compound of the present invention as an intravenous injection for an adult, it is preferable that a dose of 0.01 to 10 mg is administered 2 to 5 times a day. In the case of using a compound of the present invention as a medicine for intestinal administration for an adult, it is preferable that a dose of 1 to 100 mg is administered 1 to 3 times a day. It is more preferable to appropriately increase or decrease the dose depending upon the age, the condition of the disease and the condition of the patient.

When a compound of the present invention is formed into a medicine, at least one compound represented by the general formula (I) or at least one pharmaceutically tolerable salt thereof is mixed with a pharmaceutical carrier, a shaping agent and other additives. The carrier may be either a solid or a liquid. Examples of a solid carrier are lactose, white clay (kaolin), sucrose, crystalline cellulose, cornstarch, talc, agar, pectin, acacia gum, stearic acid, magnesium stearate, lecithin and sodium chloride.

Examples of a liquid carrier are syrup, glycerin, peanut oil, polyvinyl pyrrolidone, olive oil, ethanol, benzyl alcohol, propylene glycol, and water.

Such a medicine may be used in various forms. In the case of using a solid carrier, a medicine may be prepared in the form of tablets, powder, hard gelatin capsules, suppositories or troche. The amount of solid carrier may be varied in a wide range, but it is preferably about 1 mg to 1 g.

In the case of using a liquid carrier, a medicine may be prepared in the form of syrup, emulsion, soft gelatin capsule, sterile injection contained in an ampule or the like, or aqueous or nonaqueous suspension.

The present invention will be explained in more detail hereinunder with reference to the following examples. It is however, to be understood that the present invention is not restricted thereto and any modification is possible within the scope of the present invention.

[EXAMPLES]

Example 1

Synthesis of
(R)-1-(α-phenylethylamino)-4-cyclohexylphthalazine
(Compound No. 1 in Table 1)

10.0 g of phthalic anhydride was dissolved in 200 ml of tetrahydrofuran, and 40 ml of cyclohexylmagnesium chloride (2.0M, ether solution) was added dropwise to the solution at −50° C. After stirring the solution at the same temperature for 1 hour, the reaction solution was poured into 0.5-N hydrochloric acid, and extracted with chloroform. After the organic layer was dried over magnesium sulfide, it was purified by silica gel chromatography (eluent: chloroform-methanol) to obtain 12.0 g of o-(cyclohexanoyl) benzoic acid.

12.0 g of o-(cyclohexanoyl) benzoic acid and 3.1 g of hydrazine hydrate were dissolved in 60 ml of ethanol, and the solution was refluxed for 4 hours. Ethanol was distilled off and the remaining solution was crystallized by adding ether, thereby obtaining 7.5 g of 4-cyclohexyl-1-phthalazinone.

1.0 g of 4-cyclohexyl-1-phthalazinone and 5 ml of phosphorus oxychloride were dissolved in 10 ml of dichloroethane, and the solution was stirred at 100° C. for 4 hours. The reaction solution was distilled off, and a 1-N aqueous NaOH solution was added thereto under cooling with ice. The solution was extracted with chloroform and dried over magnesium sulfide. The solvent was then distilled off, thereby obtaining 1.1 g of 1-chloro-4-cyclo-hexylphthalazine.

1.1 g of 1-chloro-4-cyclohexylphthalazine and 1.6 g of D-α-phenylethylamine were dissolved in N-methylpyrrolidone, and the solution was stirred at 140° C. for 6 hours. After cooling the solution, an aqueous 5% NaOH solution was added to the solution, and the resultant solution was extracted with chloroform. The organic layer was dried, concentrated, purified by silica gel chromatography (eluent: hexane, chloroform, ethyl acetate), and recrystallized from ether to obtain 1.05 g of (R)-1-(α-phenylethylamino)-4-cyclohexylphthalazine.

Melting point: 162.5° to 164.0° C.

Examples 2 to 38

Compounds of Examples 2 to 38 shown in Table 6 were synthesized in accordance with the method in Example 1.

Example 39

Synthesis of
(R)-1-(α-phenylethylamino)-4-(3-thienyl)
phthalazine (Compound No. 207 in Table 1)

35 ml of normal butyllithium (1.5M, hexane solution) was dissolved in 50 ml of ether, and 6.0 g of 3-bromthiophene was added dropwise to the solution at −70° C. Separately from this, 5.5 g of phthalic anhydride was dissolved in 80 ml of tetrahydrofuran, and the lithium reagent obtained above wad added dropwise to this solution at −70° C.

After stirring the solution at the same temperature for 1 hour, the reaction solution was poured into 0.5-N hydrochloric acid, and extracted with chloroform. After the organic layer was dried over magnesium sulfide, it was purified by silica gel chromatography (eluent: chloroform-methanol) to obtain 1.8 g of o-(3-thenoyl)benzoic acid.

1.8 g of o-(3-thenoyl)benzoic acid and 580 mg of hydrazine hydrate were dissolved in 20 ml of ethanol, and the solution was refluxed for 4 hours. After cooling the solution, it was crystallized by adding ether, thereby obtaining 910 mg of 4-(3-thienyl)-1-phthalazinone.

500 mg of 4-(3-thienyl)-1-phthalazinone and 3 ml of phosphorus oxychloride were dissolved in 6 ml of dichloroethane, and the solution was stirred at 100° C. for 4 hours. The reaction solution was distilled off, and a 1-N aqueous NaOH solution was added thereto under cooling with ice. The solution was extracted with chloroform and dried over magnesium sulfide. The solvent was then distilled off, thereby obtaining 515 mg of 1-chloro-4-(3-thienyl)phthalazine.

510 mg of 1-chloro-4-(3-thienyl)phthalazine and 790 mg of D-α-phenylethylamine were dissolved in 2 ml of N-methylpyrrolidone, and the solution was stirred at 140° C. for 6 hours. After cooling the solution, an aqueous 5% NaOH solution was added to the solution, and the resultant solution was extracted with chloroform. The organic layer was dried, concentrated, purified by silica gel chromatography (eluent: hexane, chloroform, ethyl acetate), and recrystallized from ether to obtain 492 mg of (R)-1-(α-phenylethylamino)-4-(3-thienyl)phthalazine.

Melting point: 144.0° to 146.0° C.

Examples 40 and 41

Compounds of Examples 40 and 41 shown in Table 6 were synthesized in accordance with the method in Example 39.

Example 42

Synthesis of (R)-1-(α-phenylethylamino)-4-(4-methyl-2-thienyl)phthalazine (Compound No. 189 in Table 1)

1.90 g of phthalic anhydride and 3.58 g of aluminum chloride were dissolved in 40 ml of dichloroethane, and 2-bromo-3-methylthiophene was added dropwise to the solution at room temperature. After stirring the solution for 4 hours, the reaction solution was poured into a 1-N hydrochloric acid under cooling with ice, and extracted with chloroform. By purifying the extract by silica gel chromatography (eluent: chloroform, ethyl acetate), 1.70 g of o-(5-bromo-2-thenoyl)benzoic acid was obtained.

1.70 g of o-(5-bromo-2-thenoyl)benzoic acid and hydrazine hydrate were dissolved in 40 ml of ethanol, and the solution was refluxed for 4 hours. After cooling the solution, it was crystallized by adding ether, thereby obtaining 315 mg of 4-(5-bromo-4-methyl-2-thienyl)-1-phthalazinone.

300 mg of 4-(5-bromo-4-methyl-2-thienyl)-1-phthalazinone, 500 mg of 5% palladium carbon (Pd-C) and 1 ml of concentrated hydrochloric acid were added to 50 ml of ethanol, and hydrogen gas was reacted with the resulting mixture under ordinary pressure. After the end of the reaction, the mixture was filtered, and the filtrate was concentrated to obtain 205 mg of 4-(methyl-2-thienyl)phthalazinone.

200 mg of 4-(4-methyl-2-thienyl)phthalazinone and 2 ml of phosphorus oxychloride were dissolved in 4 ml of dichloroethane, and the solution was stirred at 100° C. for 4 hours. The reaction solution was distilled off, and a 1-N aqueous NaOH solution was added thereto under cooling with ice. The solution was extracted with chloroform, dried and concentrated to obtain 206 mg of 1-chloro-4-(4-methyl-2-thienyl)phthalazine.

200 mg of 1-chloro-4-(4-methyl-2-thienyl)phthalazine and 100 mg of D-α-phenylethylamine were dissolved in 2 ml of N-methylpyrrolidone, and the solution was stirred at 140° C. for 8 hours. After the solution was subjected to after-treatment, it was purified by column chromatography, thereby obtaining 25 mg of (R)-1-(α-phenylethylamino)-4-(4-methyl-2-thienyl)phthalazine.

Melting point: 118.5° to 121.0° C.

Examples 43 and 44

Compounds of Examples 43 and 44 shown in Table 6 were synthesized in accordance with the method in Example 42.

Example 45

Synthesis of (R)-1-(α-cyclohexylethylamino)-4-(2-furyl)phthalazine (Compound No. 237 in Table 1)

3.4 g of furan was dissolved in 30 ml of tetrahydrofuran, and the solution was added dropwise to 34 ml of normal butyllithium (1.6M, hexane solution) at –40° C. After stirring the resultant solution at 0° C. for 4 hours, the lithium reagent was added dropwise to a solution of 7.4 g of phthalic anhydride in 100 ml of tetrahydrofuran at –70° C. After stirring the solution at the same temperature for 1 hour, the reaction solution was poured into 0.5-N hydrochloric acid, and extracted with chloroform. By purification by column chromatography (eluent: chloroform, methanol), 2.0 g of o-(2-furoyl) benzoic acid was obtained.

2.0 g of o-(2-furoyl) benzoic acid and 690 mg of hydrazine hydrate were dissolved in 30 ml of ethanol, and the solution was refluxed for 4 hours.

After cooling the solution, it was crystallized by adding ether, thereby obtaining 1.0 g of 4-(2-furyl)-1-phthalazinone.

1.0 g of 4-(2-furyl)-1-phthalazinone and 5 ml of phosphorus oxychloride were dissolved in 5 ml of dichloroethane, and the solution was stirred at 100° C. for 3 hours. The reaction solution was distilled off, and a 1-N aqueous NaOH solution was added thereto under cooling with ice. The solution was extracted with chloroform, dried and concentrated to obtain 910 mg of 1-chloro-4-(2-furyl)phthalazine.

300 mg of 1-chloro-4-(2-furyl)phthalazine and 495 mg of R-cyclohexylethylamine were dissolved in 2 ml of N-methylpyrrolidone, and the solution was stirred at 150° C. for 8 hours. After the solution was subjected to after-treatment, it was purified by column chromatography, thereby obtaining 135 mg of (R)-1-(α-cyclohexylethylamino)-4-(3-furyl)phthalazine.

Melting point: 152.0° to 153.0° C.

Example 46

Synthesis of 1-(1-imidazolyl)-4-(2-furyl)phthalazine (Compound No. 241 in Table 1)

300 mg of 1-chloro-4-(2-furyl)phthalazine and 707 mg of imidazol were dissolved in 2 ml of N-methylpyrrolidone, and the solution was stirred at 150° C. for 10 hours. After solution was subjected to after-treatment, it was purified by column chromatography, thereby obtaining 14.5 mg of 1-(1-imidazolyl)-4-(2-furyl)phthalazine.

Melting point: 151.0° to 152.5° C.

Examples 47 to 59

Compounds of Examples 47 to 59 and 59' shown in Table 6 were synthesized in accordance with the method in Example 46.

Example 60

Synthesis of (R)-1-(1-cyclohexylethylamino)-4-phenylphthalazine (R Compound of Compound No. 431 in Table 1)

722 mg (3.0 mmol) of 1-chloro-4-phenylphthalazine and 1.15 g (9.0 mmol) of (R)-(−)-1-cyclohexylethylamine were added to 2 ml of N-methylpyrrolidone, and the resultant mixture was stirred at 120° to 130° C. for 6 hours under heating. After the end of the reaction, the mixture was cooled. 20 ml of an aqueous 5% NaOH solution was added to the mixture and the solution was extracted with chloroform. The organic layer was dried over $MgSO_4$, concentrated, purified by silica gel chromatography (eluent: ethyl acetate:hexane:chloroform=1:3:1) and recrystallized from ether-chloroform, thereby obtaining 751 mg of (R)-1-(1-cyclohexylethylamino)-4-phenylphthalazine.

Melting point: 164.0° to 167.0° C.

Examples 61 to 68

Compounds of Examples 61 to 68 shown in Table 6 were synthesized in accordance with the method in Example 60.

TABLE 6

| Comp. of Ex. No. (Comp. No. in Table 1) | m.p. (°C.) |
| --- | --- |
| 2 (No. 2) | 178.5–180.0 |
| 3 (No. 34) | 182.0–184.0 |
| 4 (No. 44) | 172.0–174.5 |
| 5 (No. 40) | 221.5–222.0 |
| 6 (No. 58) | amorphous |
| 7 (No. 23) | amorphous |
| 8 (No. 27) | 165.0–170.0 |
| 9 (No. 67) | 121.0–122.0 |
| 10 (No. 75) | 125.0–125.5 |
| 11 (No. 91) | 178.0–179.0 |
| 12 (No. 316) | amorphous |
| 13 (No. 329) | amorphous |
| 14 (No. 301) | 181.0–184.0 |
| 15 (No. 331) | 152.0–153.5 |
| 16 (No. 161) | amorphous |
| 17 (No. 162) | 107.0–109.0 |
| 18 (No. 167) | 125.0–130.0 |
| 19 (No. 177) | 177.0–180.0 |
| 20 (No. 178) | 188.0–189.0 |
| 21 (No. 168) | amorphous |
| 22 (No. 174) | 139.0–145.0 |
| 23 (No. 169) | 109.0–110.5 |
| 24 (No. 170) | 132.5–135.5 |
| 25 (No. 173) | oil |
| 26 (No. 150) | amorphous |
| 27 (No. 152) | amorphous |
| 28 (No. 115) | 140.0–141.0 |
| 29 (No. 116) | 139.5–143.0 |
| 30 (No. 118) | 133.0–135.0 |
| 31 (No. 120) | 119.0–121.5 |
| 32 (No. 131) | 198.5–201.0 |
| 33 (No. 125) | 164.0–165.0 |
| 34 (No. 137) | 88.0–92.0 |
| 35 (No. 138) | amorphous |
| 36 (No. 141) | 162.0–163.5 |
| 37 (No. 142) | 154.0–155.0 |
| 38 (No. 147) | 194.0–195.5 |
| 40 (No. 208) | 152.0–156.0 |

TABLE 6-continued

| Comp. of Ex. No. (Comp. No. in Table 1) | m.p. (°C.) |
| --- | --- |
| 41 (No. 181) | 178.0–179.5 |
| 43 (No. 197) | 134.0–136.5 |
| 44 (No. 215) | 149.0–152.5 |
| 47 (No. 354) | 130.0–134.0 |
| 48 (No. 346) | 168.0–171.0 |
| 49 (No. 362) | 160.0–161.0 |
| 50 (No. 370) | 170.0–174.0 |
| 51 (No. 371) | 199.5–201.0 |
| 52 (No. 373) | 183.0–185.5 |
| 53 (No. 375) | 192.0–193.5 |
| 54 (No. 386) | 195.0–197.0 |
| 55 (No. 380) | 151.0–152.5 |
| 56 (No. 396) | 110.0–116.0 |
| 57 (No. 403) | 85.0–90.0 |
| 58 (No. 410) | 118.0–119.0 |
| 59 (No. 293) | 135.0–136.5 |
| 59' (No. 283) | 168–175 decomposition |
| 61 (No. 431) | 165.0–167.0 |
| 62 (No. 432) | amorphous |
| 63 (No. 433) | 139.0–145.0 |
| 64 (No. 434) | 147.0–150.0 |
| 65 (No. 445) | amorphous |
| 66 (No. 454) | amorphous |
| 67 (No. 489) | 158.0–159.5 |
| 68 (No. 501) | 191.0–192.0 |

In Table 6, the compounds in Examples 7, 9, 10, 11, 12, 13, 14, 15, 28, 34, 41, 43, 44, 47, 48, 49, 50, 56, 57, 58, 59, 65 and 66 are R compounds, the compound in Example 61 is an S compound, and the compounds in Examples 62, 63, 64, 67 and 68 are RS compounds. The compound in Example 8 is a hydrochloride and that in Example 59' is a fumarate.

Example 69

Synthesis of (R)-4-(1-phenylethylamino)-7-(2-thienyl) thieno[2 3-d]pyridazine (Compound No. 523 in Table 2)

2.0 g of 2-(3-thienyl)-4,4-dimethyloxazoline was dissolved in 50 ml of ether, and 10 ml of s-butyllithium (1.3M, cyclohexane solution) was added dropwise thereto at −70° C. The solution was stirred for 1 hour. The reaction solution was added dropwise to a solution of 2.4 g of 2-thenoyl chloride in 50 ml of tetrahydrofuran at −78° C., and the solution was stirred for 30 minutes. Thereafter, 1 ml of methanol was added to the solution, and the reaction solution was concentrated. After adding water thereto, the solution was extracted with chloroform. The chloroform layer was dried and concentrated, and the residue was purified by silica gel chromatography to obtain 2.8 g of 2-(2-thenoyl)-3-(4,4-dimethyl-2-oxazoline-2-yl)thiophene.

2.8 g of 2-(2-thenoyl)-3-(4,4-dimethyl-2-oxazoline-2-yl)thiophene was added to a solution of 30 ml of concentrated hydrochloric acid, 20 ml of water and 20 ml of dioxane, and the solution was stirred at 100° C. for 8 hours. After cooling the solution, an aqueous NaCl solution was added thereto. The resultant solution was extracted with chloroform and dried. After the solvent was distilled off, the residue was purified by silica gel chromatography to obtain 0.70 g of 2-(2-thenoyl)-3-thiophene carboxylic acid.

0.70 g of 2-(2-thenoyl)-3-thiophene carboxylic acid and 0.22 g of hydrazine hydrate were dissolved in 20 ml of ethanol, and the solution was refluxed for 5 hours. After cooling the solution, it was crystallized by adding ether, thereby obtaining 0.61 g of 7-(2-thienyl)thieno[2,3-d]-pyridazine-4(5H)-one.

0.30 g of 7-(2-thienyl)thieno[2,3-d]pyridazine-4(5H)-one and 0.30 g of phosphorus oxychloride were dissolved in 10 ml of dichloroethane, and the solution was stirred at 100° C. for 10 hours. The reaction solution was concentrated, and a 1-N aqueous KOH solution was added thereto under cooling with ice. The solution was extracted with chloroform and dried. The solvent was distilled off, thereby obtaining 0.31 g of 4-chloro-7-(2-thienyl)thieno-[2,3-d]pyridazine.

0.31 g of 4-chloro-7-(2-thienyl)thieno[2,3-d]pyridazine and 0.48 g of (R)-1-phenylethylamine was dissolved in 2 ml of N-methylpyrrolidone, and the solution was stirred at 150° C. for 10 hours. After cooling the solution, an aqueous 5% KOH solution was added thereto, and the solution was extracted with chloroform and dried. The solvent was distilled off, and the residue was purified by silica gel chromatography to obtain 0.27 g of (R)-4-(1-phenylethylamino)-7-(2-thienyl)-thieno[2,3-d]pyridazine.

Melting point: 215.5° to 216.5° C.

Examples 70 to 94

Compounds of Examples 70 to 94 shown in Tables 7, 8 and 9 were synthesized in accordance with the method in Example 69.

TABLE 7

| Comp. of Ex. No. (Comp. No. in Table 2) | m.p. (°C.) |
| --- | --- |
| 70 (No. 513) | 187.5–188 |
| 71 (No. 514) | 162–163 |
| 72 (No. 515) | 205–206 |
| 73 (No. 516) | 184–186 |
| 74 (No. 517) | 183–184.5 |
| 75 (No. 518) | 165.0–166.0 |
| 76 (No. 519) | amorphous |
| 77 (No. 520) | amorphous |
| 78 (No. 521) | 154.5–156.0 |
| 79 (No. 522) | 89.0–95.0 |
| 80 (No. 524) | 215.5–216.5 |
| 81 (No. 525) | |

TABLE 8

| Comp. of Ex. No. (Comp. No. in Table 3) | m.p. (°C.) |
| --- | --- |
| 82 (No. 526) | 82–85 |
| 83 (No. 527) | |
| 84 (No. 528) | |
| 85 (No. 529) | |
| 86 (No. 530) | 140–147 |
| 87 (No. 531) | 130–132 |
| 88 (No. 532) | 129–130 |
| 89 (No. 533) | 130–132 |
| 90 (No. 534) | amorphous |
| 91 (No. 535) | 78–85 |
| 92 (No. 536) | amorphous |

In Tables 7 and 8, the compounds in Examples 70, 75, 78, 79, 82, 88, 90, 91 and 92 are R compounds, and the compound in Example 83 is an S compound.

TABLE 9

| Comp. of Ex. No. (Comp. No. in Table 4) | m.p. (°C.) |
| --- | --- |
| 93 (No. 537) | 172–175 |

TABLE 9-continued

| Comp. of Ex. No. (Comp. No. in Table 4) | m.p. (°C.) |
| --- | --- |
| 94 (No. 538) | 152–154 |

In Table 9, the compounds in Examples 93 and 94 are R compounds.

Example 95

Synthesis of (R)-4-(1-cyclohexylethylamino)-7-phenyl-furano[2,3-d]pyridazine (Compound No. 539 in Table 5)

5.96 g of diisopropylamine was dissolved in 50 ml of tetrahydrofuran, and 35 ml of n-butyllithium (1.6M) was added dropwise thereto at 0° C., and then a solution of 3.0 g of 3-furoic acid in 20 ml of tetrahydrofuran was added dropwise thereto at −78° C. The reaction solution was added dropwise to a solution of 5.6 g of benzoyl chloride in 50 ml of tetrahydrofuran at −78° C., and the resultant solution was stirred for 30 minutes. After diluted hydrochloric acid was added, the mixed solution was extracted with chloroform and the extract was purified by silica gel chromatography to obtain 3.2 g of 2-benzoyl-3-froic acid.

3.0 g of 2-benzoyl-3-froic acid and 0.76 g of hydrazine hydrate were dissolved in 30 ml of ethanol, and the solution was refluxed for 3 hours. After cooling the solution, it was concentrated, and the residue was purified by silica gel chromatography to obtain 0.25 g of 7-phenyl-furano[2,3-d]pyridazine-4-(5H)-one.

0.15 g of 7-phenyl-furano[2,3-d]pyridazine-4-(5H)-one and 10 ml of phosphorus oxychloride were dissolved in 10 ml of dichloroethane, and the solution was stirred at 100° C. for 3 hours. The reaction solution was concentrated, and a 1-N aqueous KOH solution was added thereto under cooling with ice. The solution was extracted with chloroform and dried. The solvent was distilled off, thereby obtaining 0.10 g of 4-chloro-7-phenyl-furano[2,3-d]pyridazine.

0.10 g of 4-chloro-7-phenyl-furano[2,3-d]pyridazine and 0.165 g of (R)-1-cyclohexylethylamine was dissolved in 1 ml of N-methylpyrrolidone, and the solution was stirred at 140° C. for 6 hours. After cooling the solution, an aqueous 5% KOH solution was added thereto, and the solution was extracted with chloroform. By purifying the extract by silica gel chromatography, 0.061 g of (R)-4-(1-cyclohexylethylamino)-7-phenyl-furano[2,3-d]pyridazine was obtained.

Melting point: 126° to 130° C.

Experiment 1

Inhibitory Effects of 3,6-Disubstituted Pyridazine Derivatives on Platelet Agglutination of Rats Ex Vitro Arterial blood of a rat was centrifuged to obtain platelet rich plasma. 5 ml of a medicinal solution was added to 250 µl of the platelet rich plasma, and the mixture was incubated for 2 minutes. Thereafter, 3 µg of collagen (produced by Hormon-Chemie) was added to the mixture as a platelet agglutination inducer, and changes in the platelet agglutination were observed and recorded by a 2-channel platelet agglutination degree measuring instrument (Model DP247E, produced by Sienco) for 10 minutes.

The platelet agglutination inhibitory ratio was calculated from the following formula:

Inhibitory ratio=$(Tc-Ts)/Tc \times 100$

Tc: Agglutination degree when only a solvent was added

Ts: Agglutination degree when a medicinal solution was added

The inhibitory ratios of each compound having different mol concentrations are shown in Tables 10 to 14.

Experiment 2

Inhibitory Effects of 3,6-Disubstituted Pyridazine Derivatives on Platelet Agglutination of Rats In Vivo (Oral Administration)

A rat group consisting of 8 male Wistar-ST rats each weighing about 250 g was tested. Each compound was suspended in aqueous 1% tragacanth solution. The thus-prepared suspension was orally administered to each rat at a dose of 4 ml/kg. One hour after, blood was collected from each carotid artery through a cannula into a plastic test tube containing 3.8% sodium citrate in amount corresponding to $\frac{1}{10}$ of the volume of the test tube) and the mixture was stirred. Thereafter, the mixture was centrifuged at 200×g rpm for 15 minutes, and the supernatant liquid was taken as platelet rich plasma (PRP). The residue was further centrifuged at 2000×g rpm for 15 minutes, and the supernatant liquid was collected as platelet poor plasma (PPP) and used for measurement of the platelet agglutinating ability. The platelet agglutinating ability was measured by a 2-channel platelet agglutination degree measuring instrument (Model DP247E, produced by Sienco), and recorded by a 2-pen recorder.

Collagen (produced by Hormon-Chemie) having a concentration of 7 to 10 µg/ml was used as a platelet agglutination inducer.

The platelet agglutination inhibitory ratio was calculated from the following formula:

Inhibitory ratio=$(A-B)/A \times 100$ (%)

A: Agglutination degree in the group (controlled group) to which only a solution of 1% tragacanth was administered B: Agglutination degree in the group to which the tragacanth solution containing a compound was administered The results are shown in Tables 10 to 14.

TABLE 10

| Comp. of Ex. No. (Comp. No. in Table 1) | in vitro Inhibitory ratio (%) | | | ex vivo Inhibitory ratio (%) (p.o) |
|---|---|---|---|---|
| | $10^{-7}$M | $3 \times 10^{-7}$M | $10^{-6}$M | 1 mg/kg |
| 1 (No. 1) | 89.2 | 97.1 | | |
| 2 (No. 2) | 56.0 | 96.0 | | |
| 3 (No. 34) | | 18.4 | 100 | |
| 4 (No. 44) | | 100 | | |
| 5 (No. 40) | | | 51.8 | |
| 6 (No. 58) | 35.2 | 58.3 | 98.0 | |
| 7 (No. 23) | 96.1 | | | |
| 9 (No. 67) | | | 23.8 | |
| 10 (No. 75) | | | 36.8 | |
| 11 (No. 91) | | | 56.2 | |
| 12 (No. 316) | | | 17.9 | |
| 13 (No. 329) | | | 22.5 | |
| 14 (No. 301) | | 8.2 | 75.8 | |
| 15 (No. 331) | | 13.5 | 88.1 | |
| 16 (No. 161) | 30.8 | 32.7 | 100 | |
| 17 (No. 162) | 27.5 | 80.4 | 100 | |

TABLE 10-continued

| Comp. of Ex. No. (Comp. No. in Table 1) | in vitro Inhibitory ratio (%) | | | ex vivo Inhibitory ratio (%) (p.o) |
|---|---|---|---|---|
| | $10^{-7}$M | $3 \times 10^{-7}$M | $10^{-6}$M | 1 mg/kg |
| 18 (No. 167) | 100 | | | 10.5 |
| 19 (No. 177) | 46.9 | 100 | | |
| 20 (No. 178) | 100 | | | 48.9 |
| 21 (No. 168) | 100 | | | 42.5 |
| 22 (No. 174) | 100 | | | 38.5 |
| 23 (No. 169) | 100 | | | 15.3 |
| 24 (No. 170) | 100 | | | 41.5 |
| 25 (No. 173) | 0 | 5 | 57.5 | |
| 26 (No. 150) | 100 | | | 38.5 |
| 27 (No. 152) | 100 | | | 53.6 |
| 28 (No. 115) | 100 | | | |
| 29 (No. 116) | 100 | | | 56.2 |
| 30 (No. 118) | 68.0 | 94.6 | | |
| 31 (No. 120) | | 52.2 | 91.0 | |
| 32 (No. 131) | 52.5 | 73.6 | 88.5 | |
| 33 (No. 125) | | 14.6 | 78.9 | |
| 34 (No. 137) | 98.6 | | | |
| 35 (No. 138) | 47.6 | 97.7 | | |
| 36 (No. 141) | 49.6 | 85.1 | | |
| 37 (No. 142) | | 49.4 | 73.6 | |
| 38 (No. 147) | 49.4 | 92.6 | | |
| 39 (No. 207) | 94.9 | | | |
| 40 (No. 208) | 91.2 | 100 | | |
| 41 (No. 181) | 55.8 | 91.3 | | |
| 42 (No. 189) | 96.3 | | | |
| 43 (No. 197) | | 55.0 | 85.8 | |
| 44 (No. 215) | | 16.2 | 52.6 | |
| 45 (No. 237) | 98.6 | | | |
| 46 (No. 241) | | 40.6 | 66.5 | |
| 47 (No. 354) | | 28.6 | 91.5 | |
| 48 (No. 346) | 62.7 | 91.9 | | 25.3 |
| 49 (No. 362) | | 81.4 | 92.1 | |
| 50 (No. 370) | | 37.6 | 94.5 | |
| 51 (No. 371) | | | 13.4 | |
| 52 (No. 373) | | | 0.4 | |
| 53 (No. 375) | | | 8.5 | |
| 54 (No. 386) | | | 35.5 | |
| 55 (No. 380) | | | 10.1 | |
| 56 (No. 396) | | | 3.8 | |
| 57 (No. 403) | | | 44.1 | |
| 58 (No. 410) | | | 2.5 | |
| 59 (No. 293) | | | 27.7 | |
| 60 (No. 431) (R) | 94.3 | | | 51.3 |
| 61 (No. 431) (S) | 30.2 | 94.4 | | |
| 62 (No. 432) | | 61.3 | 83.5 | |
| 63 (No. 433) | | 90.3 | | |
| 65 (No. 445) | 93.2 | | | |
| 67 (No. 489) | 61.0 | | | 41.1 |
| 68 (No. 501) | 95.0 | | | |

In Table 10, the compounds in Examples 1, 7, 9, 10, 11, 12, 13, 14, 15, 28, 34, 39, 41, 42, 43, 44, 45, 47, 48, 49, 50, 56, 57, 58, 59, 60 and 65 are R compounds, the compound in Example 61 is an S compound, and the compounds in Examples 62, 63, 67 and 68 are RS compounds.

TABLE 11

| Comp. of Ex. No. (Comp. No. in Table 2) | in vitro Inhibitory ratio (%) | | | ex vivo Inhibitory ratio (%) (p.o) |
|---|---|---|---|---|
| | $10^{-7}$M | $3 \times 10^{-7}$M | $10^{-6}$M | 1 mg/kg |
| 69 (No. 523) | 50.8 | 95.2 | | |
| 70 (No. 513) | 95.2 | | | |
| 71 (No. 514) | 30.7 | 98.6 | | |
| 72 (No. 515) | 5.1 | 95.3 | | |
| 73 (No. 516) | 42.8 | 95.6 | | |
| 74 (No. 517) | 73.4 | 93.5 | | |
| 75 (No. 518) | 94.5 | | | 50.2 |

TABLE 11-continued

| Comp. of Ex. No. (Comp. No. in Table 2) | in vitro Inhibitory ratio (%) | | | ex vivo Inhibitory ratio (%) (p.o) |
|---|---|---|---|---|
| | $10^{-7}$M | $3 \times 10^{-7}$M | $10^{-6}$M | 1 mg/kg |
| 79 (No. 522) | | 6.6 | 94.3 | |
| 80 (No. 524) | 100 | | | |
| 81 (No. 525) | 100 | | | |

In Table 11, the compounds in Examples 69, 70, 75 and 79 are R compounds.

TABLE 12

| Comp. of Ex. No. (Comp. No. in Table 3) | in vitro Inhibitory ratio (%) | | | ex vivo Inhibitory ratio (%) (p.o) |
|---|---|---|---|---|
| | $10^{-7}$M | $3 \times 10^{-7}$M | $10^{-6}$M | 1 mg/kg |
| 82 (No. 526) | 93.3 | | | 37.9 |
| 83 (No. 527) | | 94.3 | | |
| 84 (No. 528) | | 24.5 | 61.6 | |
| 85 (No. 529) | | | 40.7 | |
| 86 (No. 530) | | 78.2 | 90.2 | |
| 87 (No. 531) | | | 18.0 | |
| 89 (No. 533) | | 49.5 | 95.4 | |
| 90 (No. 534) | 32.7 | 94.4 | | 60.6 |

In Table 12, the compounds in Examples 82 and 90 are R compounds, and the compound in Example 83 is an S compound.

TABLE 13

| Comp. of Ex. No. (Comp. No. in Table 4) | in vitro Inhibitory ratio (%) | | | ex vivo Inhibitory ratio (%) (p.o) |
|---|---|---|---|---|
| | $10^{-7}$M | $3 \times 10^{-7}$M | $10^{-6}$M | 1 mg/kg |
| 93 (No. 537) | | 9.3 | 93.4 | |

In Table 13, the compound in Example 93 is an R compound.

TABLE 14

| Comp. of Ex. No. (Comp. No. in Table 5) | in vitro Inhibitory ratio (%) | | | ex vivo Inhibitory ratio (%) (p.o) |
|---|---|---|---|---|
| | $10^{-7}$M | $3 \times 10^{-7}$M | $10^{-6}$M | 1 mg/kg |
| 95 (No. 539) | 94.4 | 100 | | 63.1 |

In Table 14, the compound in Examples 95 is an R compound.

Experiment 3

Effects of 3,6-Disubstituted Pyridazine Derivatives on the Myocardial Infarction of a Rat Induced by the Ligation of the Left Coronary Artery A rat group consisting of 8 male SD rats each weighing 200 to 250 g was tested. Myocardial infarction was produced in accordance with a method of Selye et al. That is, each rat was fixed on an operating boar on its back, and an about 1.5 cm incision had been made through the skin along the left sternal border under weak etherization. The pericardium was broken to exteriorize the heart, and the left coronary artery was ligated at a position of 1 to 2 mm apart from the origin thereof with black blade 4-O silk suture (produced by Hama Ika Kogyo). Thereafter, the heart was restored to its original position and the chest was sutured. The air in the throacic cavity was discharged by pressing both side breast portions. After the resumption of respiration, the ST elevation in the standard limb lead II by an electrocardiograph (Model ECG-6601, produced by Nihon Koden Co.,). 24 hours after the ligation, blood was collected from the aortas at the abdomen. A fatal amount of blood was then drawn from each rat. The heart was taken out, and a tissue slice (about 2 mm thick) having an annular cross section was cut from the central portion of the heart. The tissue slice was incubated in 20 ml of 1% TTC (tryphenyl tetrazolium chloride, produced by Wako Pure Chemical Industries Limited) dissolved in 0.09M of phosphoric acid buffer (pH 8.6) at 37° C. for 20 minutes while shielding light. The tissue slice was photographed by a stereoscopic microscope to produce a color slide. The image of the tissue slice was projected on a wall surface from the color slide. The cut surface, the infarcted portion (portion not dyed with TTC) and the non-infarcted portion (portion dyed with TTC) were traced on a sheet, and the area of the infarcted portion in the whole cross section was calculated. The medicine was suspended in an aqueous 1% tragacanth solution and orally administered to each rat 60 minutes before the ligation of the left coronary artery.

The myocardial infarction inhibitory ratio was calculated from the following formula:

$$\text{Inhibitory ratio} = \frac{A - B}{A} \times 100 \, (\%)$$

A: Infarction degree in the group (controlled group) to which only a solution of 1% tragacanth was administered B: Infarction degree in the group to which the tragacanth solution containing a medicine was administered The results are shown in Table 15.

TABLE 15

| Compounds No. (table 1, 2, 3 and 4) | doses (mg/kg) | percentage of inhibition |
|---|---|---|
| 431 (R) | 1 | 68.5 |
| | 3 | 82.2 |
| Aspirin* | 100 | 10.7 |
| Ticlopidine* | 30 | 10.1 |

*anti-platelet aggregation agents

What is claimed is:

1. A 3,6-disubstituted pyridazine derivative represented by the following formula (I), an optical antipode thereof or a pharmaceutically acceptable acid-addition salt thereof:

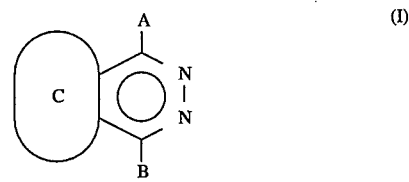

wherein

A represents a phenyl group, a thienyl group or a furyl group each of which may be substituted by an alkyl group having 1 to 4 carbon atoms;

B represents —NH—D wherein D represents

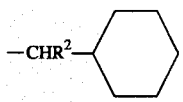

wherein R² represents an alkyl group having 1 to 4 carbon atoms; and the ring C represents a benzene ring.

2. A compound according to claim 1, wherein A represents a phenyl group and B represents

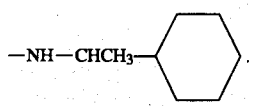

3. A pharmaceutical composition comprising a pharmaceutically effective amount of a compound according to claim 1 and a pharmaceutically acceptable carrier.

4. A method of treating a disease caused by platelet agglutination, said method comprising administering to a patient in need of said treatment a platelet agglutination inhibiting effective amount of a compound according to claim 1, and a pharmaceutically acceptable carrier.

5. A method of treating ischemic heart disease, caused by platelet agglutination, said method comprising administering to a patient in need of said treatment a platelet agglutination inhibiting effective amount of a compound according to claim 1 and a pharmaceutically acceptable carrier.

6. A method of treating myocardial infarction, caused by platelet agglutination, said method comprising administering to a patient in need of said treatment a platelet agglutination inhibiting effective amount of a compound according to claim 1 and a pharmaceutically acceptable carrier.

7. A method of treating angina pectoris, caused by platelet agglutination, said method comprising administering to a patient in need of said treatment a platelet agglutination inhibiting effective amount of a compound according to claim 1 and a pharmaceutically acceptable carrier.

8. A method of treating a cerebrovascular disorder, caused by platelet agglutination, said method comprising administering to a patient in need of said treatment a platelet agglutination inhibiting effective amount of a compound according to claim 1 and a pharmaceutically acceptable carrier.

9. A method of treating a cerebral thrombosis, caused by platelet agglutination, said method comprising administering to a patient in need of said treatment a platelet agglutination inhibiting effective amount of a compound according to claim 1 and a pharmaceutically acceptable carrier.

10. A method of treating a cerebral embolism, caused by platelet agglutination, said method comprising administering to a patient in need of said treatment a platelet agglutination inhibiting effective amount of a compound according to claim 1 and a pharmaceutically acceptable carrier.

11. A method of treating a circulation disorder, caused by platelet agglutination, said method comprising administering to a patient in need of said treatment a platelet agglutination inhibiting effective amount of a compound according to claim 1 and a pharmaceutically acceptable carrier.

12. A method of treating a peripheral circulation disorder, caused by platelet agglutination, said method comprising administering to a patient in need of said treatment a platelet agglutination inhibiting effective amount of a compound according to claim 1 and a pharmaceutically acceptable carrier.

* * * * *